US012026303B2

(12) United States Patent
Yoshimura

(10) Patent No.: US 12,026,303 B2
(45) Date of Patent: Jul. 2, 2024

(54) SIGHT LINE POSITION PROCESSING APPARATUS, IMAGE CAPTURING APPARATUS, TRAINING APPARATUS, SIGHT LINE POSITION PROCESSING METHOD, TRAINING METHOD, AND STORAGE MEDIUM

(71) Applicant: CANON KABUSHIKI KAISHA, Tokyo (JP)

(72) Inventor: Yuki Yoshimura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/378,862

(22) Filed: Jul. 19, 2021

(65) Prior Publication Data
US 2022/0026985 A1    Jan. 27, 2022

(30) Foreign Application Priority Data
Jul. 27, 2020    (JP) .................................. 2020-126725

(51) Int. Cl.
G06F 3/01        (2006.01)
G02B 27/00       (2006.01)
G02B 27/01       (2006.01)
G06V 40/19       (2022.01)

(52) U.S. Cl.
CPC ......... *G06F 3/013* (2013.01); *G02B 27/0093* (2013.01); *G02B 27/0101* (2013.01); *G06V 40/19* (2022.01); *G02B 2027/0138* (2013.01)

(58) Field of Classification Search
None
See application file for complete search history.

(56) References Cited

U.S. PATENT DOCUMENTS

| 11,367,416 | B1 * | 6/2022 | Richter | G06T 11/60 |
| 2007/0230797 | A1 * | 10/2007 | Hisanaga | G06V 40/165 |
| | | | | 382/195 |
| 2007/0276541 | A1 * | 11/2007 | Sawasaki | G05D 1/0246 |
| | | | | 700/253 |
| 2015/0178589 | A1 * | 6/2015 | Park | G06V 40/19 |
| | | | | 382/203 |
| 2017/0243485 | A1 * | 8/2017 | Rubin | H04W 4/46 |
| 2017/0256101 | A1 * | 9/2017 | Emoto | A61B 5/742 |

FOREIGN PATENT DOCUMENTS

JP    2011-120887 A    6/2011

* cited by examiner

*Primary Examiner* — Talha M Nawaz
(74) *Attorney, Agent, or Firm* — Cowan, Liebowitz & Latman, P.C.

(57) ABSTRACT

There is provided a sight line position processing apparatus. A detection unit repeatedly detects a sight line position of a user. A first determination unit determines a reliability of the sight line position detected by the detection unit. A generation unit generates a statistical sight line position by calculating a statistical value for a plurality of sight line positions detected by the detection unit. The generation unit controls a number of sight line positions used to calculate one statistical value on the basis of the reliability.

20 Claims, 9 Drawing Sheets

SIGHT LINE POSITION PROCESSING APPARATUS, IMAGE CAPTURING APPARATUS, TRAINING APPARATUS, SIGHT LINE POSITION PROCESSING METHOD, TRAINING METHOD, AND STORAGE MEDIUM

BACKGROUND OF THE INVENTION

Field of the Invention

The present invention relates to a sight line position processing apparatus, an image capturing apparatus, a training apparatus, a sight line position processing method, a training method, and a storage medium.

Description of the Related Art

Japanese Patent Laid-Open No. 2011-120887 discloses a method of selecting a rangefinding point by detecting a sight line position, within a shooting range, of a photographer who is looking into a viewfinder visual field. According to Japanese Patent Laid-Open No. 2011-120887, the rangefinding point is selected in accordance with a priority level of a plurality of rangefinding point selection means, and thus the rangefinding point can be selected according to the photographer's intentions. An image capturing apparatus described in Japanese Patent Laid-Open No. 2011-120887 includes what is known as an optical viewfinder, which makes it possible for the photographer to observe an optical image formed on a focus plate.

In recent years, there are image capturing apparatuses which, rather than optical viewfinders, have electronic viewfinders as display apparatuses which reproduce images obtained by an image sensor receiving light beams passing through an optical imaging system. Although an image capturing apparatus having an optical viewfinder has a light beam splitting means, an image capturing apparatus having an electronic viewfinder does not require a light beam splitting means, which makes it possible to perform focus detection, subject detection, and the like over a broader area within the shooting range.

Japanese Patent Laid-Open No. 2011-120887 also discloses a technique for suppressing oscillations in the sight line position by performing processing for adding a plurality of detected sight line positions to calculate an average sight line position.

When performing processing for adding a plurality of sight line positions, the calculated average sight line position is affected by past sight line positions. As such, if a predetermined number of sight line positions are uniformly added and processed, the calculated average sight line position will have a uniform delay with respect to the actual sight line position, which reduces the accuracy of sight line detection.

SUMMARY OF THE INVENTION

Having been achieved in light of such circumstances, the present invention provides a technique for improving the accuracy of sight line detection.

According to a first aspect of the present invention, there is provided a sight line position processing apparatus comprising at least one processor and/or at least one circuit which functions as: a detection unit configured to repeatedly detect a sight line position of a user; a first determination unit configured to determine a reliability of the sight line position detected by the detection unit; and a generation unit configured to generate a statistical sight line position by calculating a statistical value for a plurality of sight line positions detected by the detection unit, the generation unit controlling a number of sight line positions used to calculate one statistical value on the basis of the reliability.

According to a second aspect of the present invention, there is provided an image capturing apparatus, comprising: the sight line position processing apparatus according to the first aspect; and an image sensor.

According to a third aspect of the present invention, there is provided a sight line position processing apparatus comprising at least one processor and/or at least one circuit which functions as: a detection unit configured to repeatedly detect a sight line position of a user; and a generation unit configured to generate a statistical sight line position by calculating a statistical value for a plurality of sight line positions detected by the detection unit, the generation unit calculating the statistical value using a higher number of sight line positions when a sight line position at a first distance from a center of a display is included than when a sight line position at a second distance shorter than the first distance is included.

According to a fourth aspect of the present invention, there is provided an image capturing apparatus, comprising: the sight line position processing apparatus according to the third aspect; and an image sensor.

According to a fifth aspect of the present invention, there is provided a training apparatus comprising at least one processor and/or at least one circuit which functions as: a training unit configured to generate trained dictionary data by performing training based on a first plurality of eye area images each associated with information indicating a sight line position, wherein the training unit generates trained dictionary data that can be used for both left and right on the basis of horizontal symmetry of a right eye and a left eye in the first plurality of eye area images.

According to a sixth aspect of the present invention, there is provided a sight line position processing method executed by a sight line position processing apparatus, comprising: repeatedly detecting a sight line position of a user; determining a reliability of the sight line position detected by the detecting; and generating a statistical sight line position by calculating a statistical value for a plurality of sight line positions detected by the detecting, wherein the generating includes controlling a number of sight line positions used to calculate one statistical value on the basis of the reliability.

According to a seventh aspect of the present invention, there is provided a sight line position processing method executed by a sight line position processing apparatus, comprising: repeatedly detecting a sight line position of a user; and generating a statistical sight line position by calculating a statistical value for a plurality of sight line positions detected by the detecting, wherein the statistical value is calculated using a higher number of sight line positions when a sight line position at a first distance from a center of a display is included than when a sight line position at a second distance shorter than the first distance is included.

According to an eighth aspect of the present invention, there is provided a training method executed by a training apparatus, comprising: generating trained dictionary data by performing training based on a first plurality of eye area images each associated with information indicating a sight line position, wherein the generating generates trained dictionary data that can be used for both left and right on the basis of horizontal symmetry of a right eye and a left eye in the first plurality of eye area images.

According to a ninth aspect of the present invention, there is provided a non-transitory computer-readable storage medium which stores a program for causing a computer to execute a sight line position processing method comprising: repeatedly detecting a sight line position of a user; determining a reliability of the sight line position detected by the detecting; and generating a statistical sight line position by calculating a statistical value for a plurality of sight line positions detected by the detecting, wherein the generating includes controlling a number of sight line positions used to calculate one statistical value on the basis of the reliability.

According to a tenth aspect of the present invention, there is provided a non-transitory computer-readable storage medium which stores a program for causing a computer to execute a sight line position processing method comprising: repeatedly detecting a sight line position of a user; and generating a statistical sight line position by calculating a statistical value for a plurality of sight line positions detected by the detecting, wherein the statistical value is calculated using a higher number of sight line positions when a sight line position at a first distance from a center of a display is included than when a sight line position at a second distance shorter than the first distance is included.

According to an eleventh aspect of the present invention, there is provided a non-transitory computer-readable storage medium which stores a program for causing a computer to execute a training method comprising: generating trained dictionary data by performing training based on a first plurality of eye area images each associated with information indicating a sight line position, wherein the generating generates trained dictionary data that can be used for both left and right on the basis of horizontal symmetry of a right eye and a left eye in the first plurality of eye area images.

Further features of the present invention will become apparent from the following description of exemplary embodiments with reference to the attached drawings.

DESCRIPTION OF THE EMBODIMENTS

Figure 1:
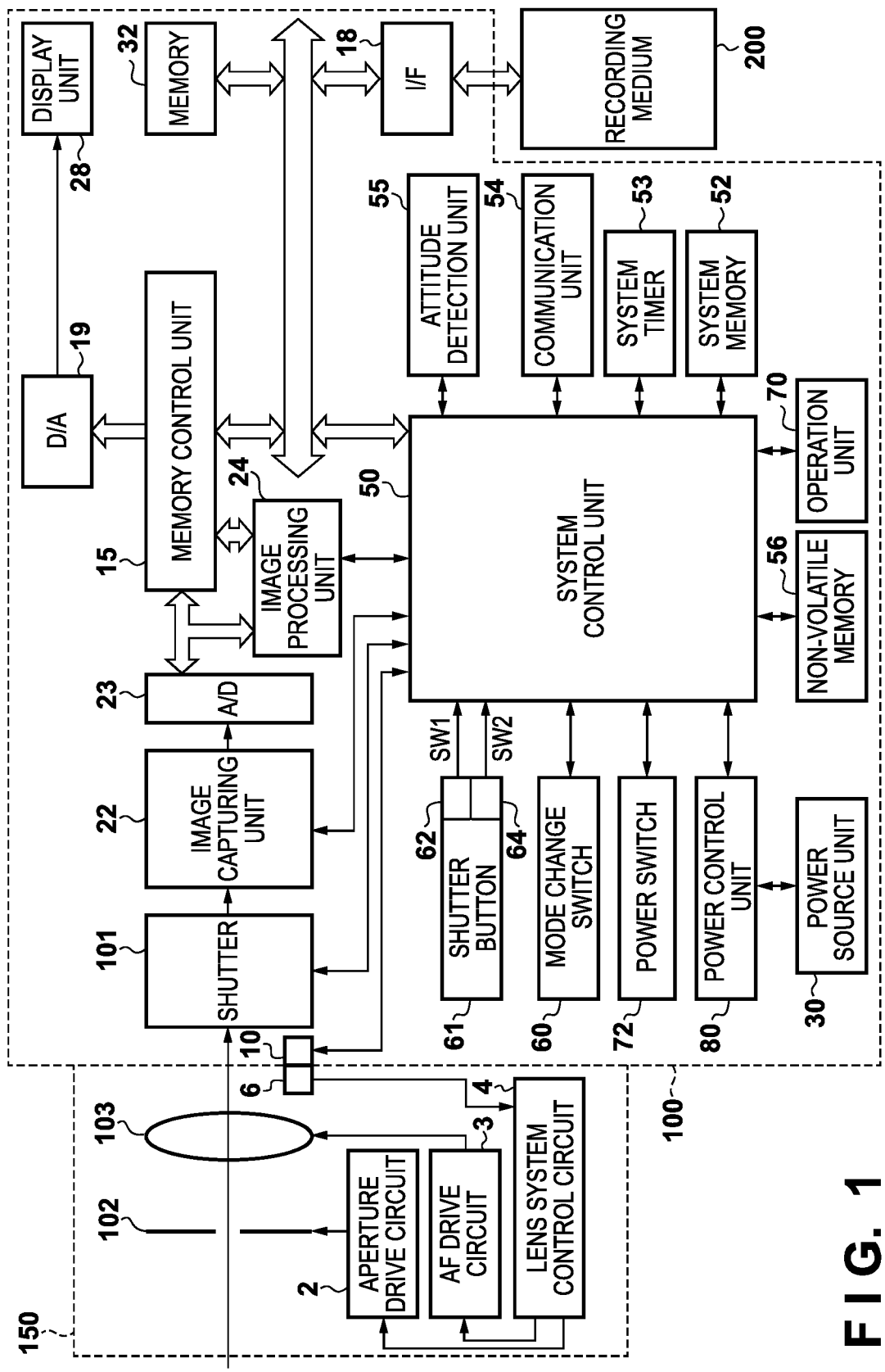
FIG. 1 is a block diagram illustrating the configuration of a digital camera 100 including a sight line position processing apparatus.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

First Embodiment

Configuration of Digital Camera 100

FIG. 1 is a block diagram illustrating the configuration of a digital camera 100 including a sight line position processing apparatus. In FIG. 1, a lens unit 150 is an interchangeable lens unit including a shooting lens, and can be attached to and removed from the digital camera 100. A lens 103 is normally constituted by a plurality of lenses, but only one lens is shown here for the sake of simplicity. A communication terminal 6 is a communication terminal through which the lens unit 150 communicates with the digital camera 100, and a communication terminal 10 is a communication terminal through which the digital camera 100 communicates with the lens unit 150. The lens unit 150 communicates with a system control unit 50 through the communication terminals 6 and 10, controls an aperture stop 102 through an aperture drive circuit 2 using an internal lens system control circuit 4, and adjusts the focus by changing the position of the lens 103 through an AF drive circuit 3.

A shutter 101 is a focal plane shutter through which the exposure time of an image capturing unit 22 can be freely controlled under the control of the system control unit 50. The image capturing unit 22 is an image sensor constituted by a CCD, a CMOS element, or the like that converts an optical image into an electrical signal. An A/D converter 23 converts analog signals into digital signals. The A/D converter 23 is used to convert analog signals output from the image capturing unit 22 into digital signals. The signal obtained from the image capturing unit 22 is used not only to capture images, but also for exposure control and focus detection control. In the image capturing unit 22, a pixel in which a photoelectric conversion unit is divided is provided for a single microlens. Dividing the photoelectric conversion unit also divides the entrance pupil, which makes it possible to obtain a phase detection signal from each photoelectric conversion unit. A captured image signal can also be obtained by adding signals from the divided photoelectric conversion unit. Such a pixel is advantageous in that the pixel can be used as both a focus detection pixel and an image capturing pixel.

Figure 2:
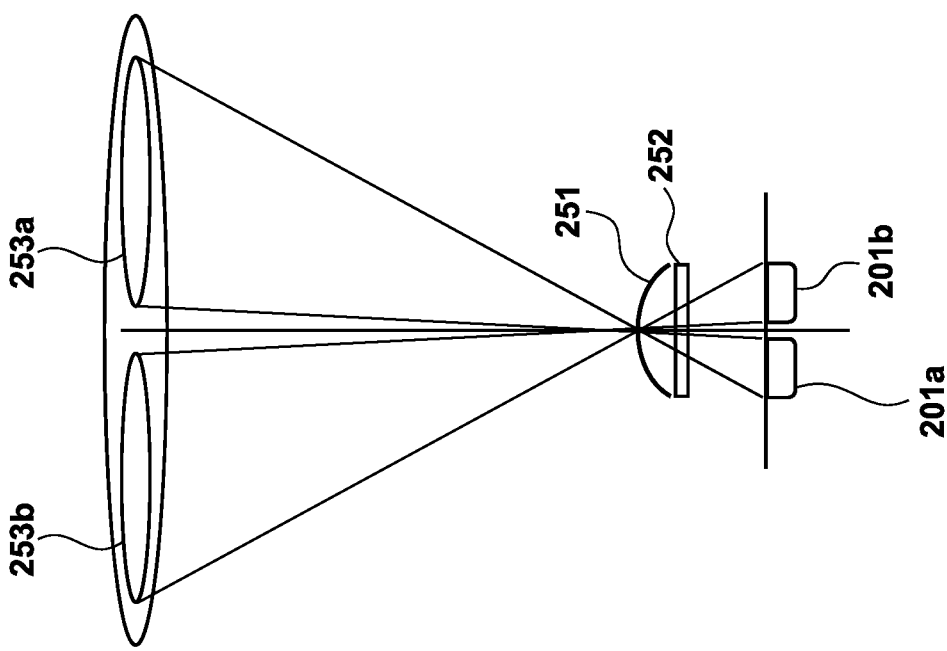
FIG. 2 is a diagram illustrating the configuration of a pixel in an image capturing unit 22, and a correspondence relationship between a pupil plane and a photoelectric conversion unit.

FIG. 2 is a diagram illustrating the configuration of a pixel in the image capturing unit 22, and a correspondence relationship between a pupil plane and a photoelectric conversion unit. 201 indicates the photoelectric conversion unit, 253 indicates the pupil plane, 251 indicates a microlens, and 252 indicates a color filter. In FIG. 2, two photoelectric conversion units 201, namely a photoelectric conversion unit 201a (a first focus detection pixel) and a photoelectric conversion unit 201b (a second focus detection pixel) are provided. Light passing through a pupil plane 253a is incident on the photoelectric conversion unit 201a, and light passing through a pupil plane 253b is incident on the photoelectric conversion unit 201b. As a result, focus detection can be performed from signals obtained from the photoelectric conversion unit 201a and the photoelectric conversion unit 201b. Additionally, a captured image signal can be generated by adding the signals obtained from the photoelectric conversion unit 201a and the photoelectric conversion unit 201b.

In the present embodiment, the pixels illustrated in FIG. 2 are provided across the entire picture plane region of the image capturing unit 22, which makes it possible to use phase detection to focus on any subject in the picture plane.

Although the descriptions in the present embodiment will be given using the above-described focus detection method, the focus detection method is not limited to this example. For example, the image capturing unit 22 may be provided with dedicated focus detection pixels, illustrated in FIG. 3 and described below, to perform focus detection. Additionally, the image capturing unit 22 may be provided only with pixels for capturing images, without being provided with pixels for focus detection, and may perform focus detection using a contrast-based method.

Figure 3:
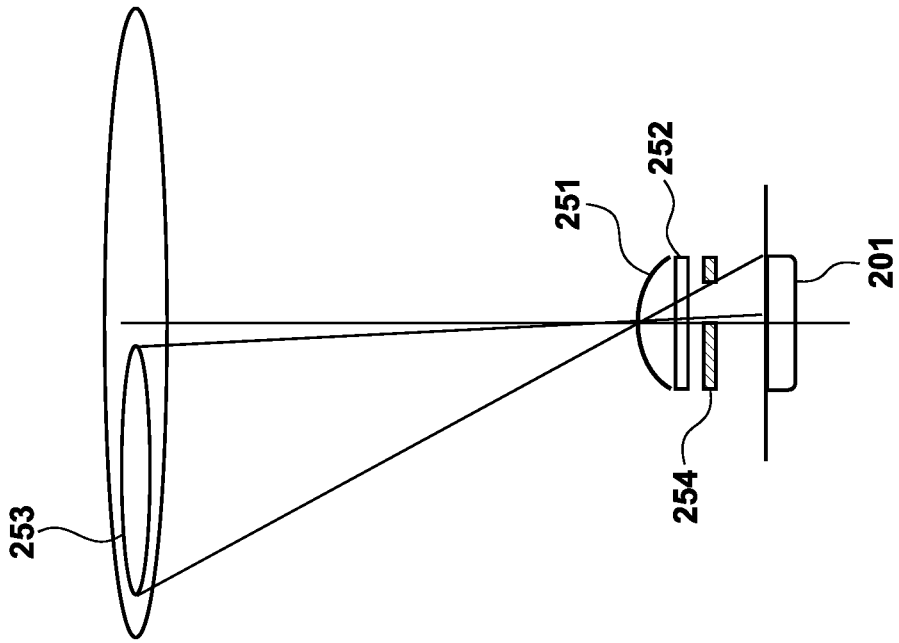
FIG. 3 is a diagram illustrating the configuration of a dedicated focus detection pixel, and a correspondence relationship between a pupil plane and a photoelectric conversion unit.

FIG. 3 is a diagram illustrating the configuration of the dedicated focus detection pixel, and a correspondence relationship between a pupil plane and a photoelectric conversion unit. Unlike the pixel illustrated in FIG. 2, the pixel illustrated in FIG. 3 is a pixel specifically for focus detection. The shape of a pupil plane 253 is determined by an opening 254. Additionally, only light passing through the pupil plane 253 is detected, and it is therefore necessary to provide an additional pixel to form a pair (a pixel which detects light from a pupil plane on the right side, not shown in FIG. 3) and obtain the focus detection signals. The dedicated focus detection pixels illustrated in FIG. 3 and image capturing pixels are provided across the entire picture plane region of the image capturing unit 22, which makes it possible to use phase detection to focus on any subject in the picture plane.

Returning to FIG. 1, an image processing unit 24 carries out predetermined pixel interpolation, resizing processing such as reduction, color conversion processing, and the like on data from the A/D converter 23 or data from a memory control unit 15. The image processing unit 24 also performs predetermined computational processing using captured image data, and a system control unit 50 performs exposure control and rangefinding control based on results obtained from these computations. A TTL (through-the-lens) AF (autofocus) process, an AE (automatic exposure) process, and an EF (flash pre-emission) process are realized as a result. The image processing unit 24 also performs predefined computations using the captured image data, performing a TTL AWB (auto white balance) process on the basis of the results thereof.

Data output from the A/D converter 23 is written into memory 32 through the image processing unit 24 and the memory control unit 15, or directly through the memory control unit 15. The memory 32 stores the image data obtained by the image capturing unit 22 and converted into digital data by the A/D converter 23, image data for display in a display unit 28, and the like. The memory 32 is provided with a storage capacity sufficient to store a predetermined number of still images, a predetermined time's worth of moving images and audio, and the like. The memory 32 also functions as image display memory (video memory).

A D/A converter 19 converts data for image display, stored in the memory 32, into an analog signal and supplies the analog signal to the display unit 28. Image data for display written into the memory 32 is thus displayed by the display unit 28 via the D/A converter 19 in this manner. The display unit 28 carries out a display in the display device, which is an LCD or the like, based on the analog signal from the D/A converter 19. An electronic viewfinder function is realized by using the D/A converter 19 to convert the digital signals A/D converted by the A/D converter 23 and stored in the memory 32 into analog signals and then sequentially transferring and displaying those signals in the display unit 28. A through-the-lens image display (live view display) can be carried out as a result. An electronic viewfinder that is viewed through an eyepiece (not shown), or a display provided on the back of the digital camera 100, may be provided as the display unit 28. Alternatively, both an electronic viewfinder and a display on the back may be provided.

Non-volatile memory 56 is electrically erasable/recordable memory, and, for example, EEPROM is used. Operational constants, programs, and the like of the system control unit 50 are stored in the non-volatile memory 56. Here, "programs" refers to programs for executing the various flowcharts according to the present embodiment, which will be described later.

The system control unit 50 controls the entire digital camera 100. The respective processes according to the present embodiment, mentioned later, are realized by executing programs recorded in the non-volatile memory 56 mentioned above. 52 indicates system memory, for which RAM is used. Operational constants and variables for the system control unit 50, programs read out from the non-volatile memory 56, and the like are loaded into the system memory 52. The system control unit 50 also carries out display control by controlling the memory 32, the D/A converter 19, the display unit 28, and the like.

A system timer 53 is a time measurement unit that measures times used in various types of control, measures the time of an internal and clock, and the like. A power switch 72 is an operation member that switches the power of the digital camera 100 on and off.

A mode change switch 60, a first shutter switch 62, a second shutter switch 64, and an operation unit 70 are operation members for inputting various types of operation instructions to the system control unit 50.

The mode change switch 60 switches the operating mode of the system control unit 50 among a still image recording mode, a moving image shooting mode, a playback mode, and the like. The still image recording mode includes an auto shooting mode, an auto scene determination mode, a manual mode, an aperture priority mode (Av mode), and a shutter speed priority mode (Tv mode). There are also various types of scene modes, a program AE mode, custom modes, and the like as shooting settings for different shooting scenes. The mode change switch 60 can be used to switch directly to any one of these modes included in a menu screen. Alternatively, the mode switch may be carried out by first switching the screen display to the menu screen using the mode change switch 60 and then using another operation member to switch to one of the modes included in the menu screen. Likewise, the moving image shooting mode may include a plurality of modes.

The first shutter switch 62 switches on partway through the operation of a shutter button 61 provided in the digital camera 100, or in other words, when the button is depressed halfway (a shooting preparation instruction), and produces a first shutter switch signal SW1. Operations such as AF (autofocus) processes, AE (automatic exposure) processes, AWB (auto white balance) processes, and EF (flash pre-emission) processes are started by the first shutter switch signal SW1.

The second shutter switch 64 turns on when the shutter button 61 is completely operated, or in other words, is fully depressed (a shooting instruction), and produces a second shutter switch signal SW2. The system control unit 50 starts a series of shooting processes, from reading out signals from the image capturing unit 22 to writing image data into a recording medium 200, in response to the second shutter switch signal SW2.

The operation unit 70 includes various types of operation members as input units for accepting operations from the user. The operation unit 70 is provided with electronic buttons, a directional key, and the like for performing menu selections mode selections, playing back captured moving images, and the like. Functions relevant for different situations are assigned to operation members in the operation unit 70, which then act as various types of function buttons, by making an operation for selecting various types of function icons displayed in the display unit 28. An end button, a return button, a next image button, a jump button, a sort button, an attribute change button, and the like are examples of the function buttons. For example, a menu screen in which various types of settings can be made is displayed in the display unit 28 when a menu button is pressed. A user can make various types of settings intuitively using the menu screen displayed in the display unit 28, along with four directional—up, down, left, and right—buttons, a set button, and the like.

Figure 4A:
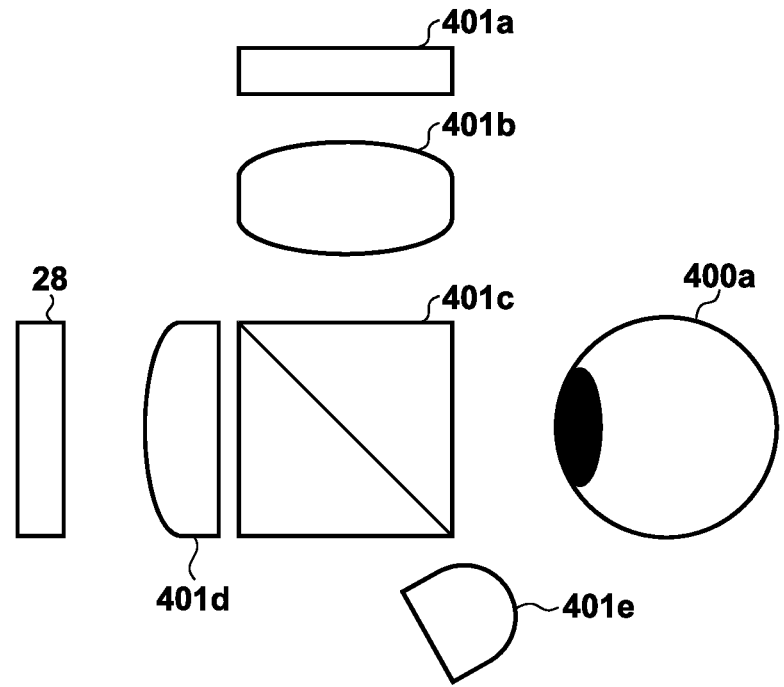
FIGS. 4A and 4B are diagrams illustrating a sight line input operation unit 401 included in an operation unit 70.
Figure 4B:
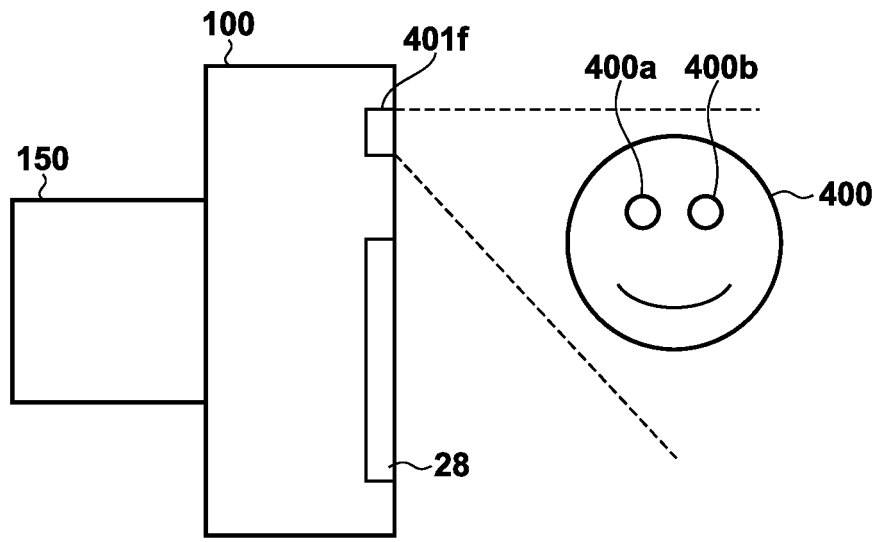

FIGS. 4A and 4B are diagrams illustrating a sight line input operation unit 401 included in the operation unit 70. The sight line input operation unit 401 is an operation member for detecting location of the display unit 28 at which the user's sight line is directed. FIG. 4A illustrates an example of the sight line input operation unit 401. The configuration of the sight line input operation unit 401 illustrated in FIG. 4A is a configuration for realizing a system in which the angle of rotation of the optical axis of an eye 400a of a user looking into the viewfinder visual field is detected and the user's sight line is detected from the detected angle of rotation, as disclosed in Japanese Patent Laid-Open No. 2011-120887. A live view image captured through the lens unit 150 is displayed in the display unit 28. 401a indicates an image sensor, 401b indicates a light receiving lens, 401c indicates a dichroic mirror, 401d indicates an ocular lens, and 401e indicates an illumination light source. Infrared light is projected onto the eye 400a by the illumination light source 401e. Infrared light reflected by the eye 400a is reflected by the dichroic mirror 401c and captured by the image sensor 401a. The captured eye image is converted into a digital signal by an A/D converter (not shown) and sent to the system control unit 50. The system control unit 50 extracts a pupil region from the captured eye image and calculates the user's sight line.

Note that the sight line detection method is not limited to the method illustrated in FIG. 4A, and a method that captures images of both eyes of the user and detects the sight line may be used as well. FIG. 4B illustrates an example of a different sight line input operation unit 401 from that in FIG. 4A. In FIG. 4B, a live view image captured through the lens unit 150 is displayed in the display unit 28, which is provided in the back of the digital camera 100. In FIG. 4B, a camera 401f that captures an image of a face 400 of the user observing the display unit 28 is provided in the back of the digital camera 100. In FIG. 4B, the dotted line indicates the angle of view captured by the camera 401f. An illumination light source (not shown) projects light onto the user's face, and the camera 401f obtains an eye image. The system control unit 50 then calculates the user's sight line on the basis of at least one of an eye 400a and an eye 400b included in the eye image. Note that the sight line detection method is not limited to this method, and any desired method capable of detecting which location of the display unit 28 the user is looking at can be used.

Returning to FIG. 1, a power control unit 80 is constituted by a battery detection circuit, a DC-DC converter, switch circuits for switching the blocks through which power passes, and the like, and detects whether or not a battery is connected, the type of the battery, the remaining battery power, and the like. The power control unit 80 also controls the DC-DC converter based on the detection results and instructions from the system control unit 50, and supplies a necessary voltage for a necessary period to the various units, including the recording medium 200.

A power source unit 30 is a primary battery such as an alkali battery, a lithium battery, or the like, a secondary battery such as a NiCd battery, a NiMH battery, a Li battery, or the like, an AC adapter, and the like. A recording medium I/F 18 is an interface for the recording medium 200 such as a memory card, a hard disk, or the like. The recording medium 200 is a recording medium for recording shot images, such as a memory card or the like, and is constituted by semiconductor memory, a magnetic disk, or the like.

A communication unit 54 is connected to an external apparatus wirelessly or over a hardwire cable, and sends and receives video signals, audio signals, and the like. The communication unit 54 can also connect to a wireless LAN (local area network), the Internet, and the like. The communication unit 54 can transmit images captured by the image capturing unit 22 (including through-the-lens image), images recorded in the recording medium 200, and the like, and can also receive image data and various other types of information from the external apparatus.

An attitude detection unit 55 detects the attitude of the digital camera 100 relative to the gravitational direction. Whether an image shot by the image capturing unit 22 is an image shot while the digital camera 100 was held horizontally or vertically can be determined on the basis of the attitude detected by the attitude detection unit 55. The system control unit 50 can add orientation information based on the attitude detected by the attitude detection unit 55 to the image file of an image captured by the image capturing unit 22, record the image in a rotated state, and the like. An accelerometer, a gyrosensor, or the like can be used as the attitude detection unit 55.

The digital camera 100 described above can capture images using center single-point AF, face AF, and the like. "Center single-point AF" refers to performing AF for a single point located in the center of the image shooting screen. "Face AF" refers to performing AF for a face within the image shooting screen, detected using a facial detection function.

The facial detection function will be described here. The system control unit 50 sends image data for facial detection to the image processing unit 24. Under the control of the system control unit 50, the image processing unit 24 applies a horizontal band pass filter to the image data. Additionally, under the control of the system control unit 50, the image processing unit 24 applies a vertical band pass filter to the processed image data. Edge components of the image data are detected using the horizontal and vertical band pass filters.

After this, the system control unit 50 performs pattern matching with respect to the detected edge components, and extracts candidate groups for the eyes, the nose, the mouth, and the ears. Then, from the extracted eye candidate groups, the system control unit 50 determines eye pairs that meet predetermined conditions (e.g., the distance between the two eyes, tilt, and the like) and narrows down the eye candidate groups to only groups having eye pairs. The system control unit 50 then detects the face by associating the narrowed-down eye candidate groups with the other parts that form the corresponding face (the nose, mouth, and ears), and passing the image through a pre-set non-face condition filter. The system control unit 50 outputs face information according to the face detection results and ends the processing. At this time, the system control unit 50 stores a feature amount such as a number of faces in the system memory 52. The method for implementing the facial detection function is not limited to the method described above, and the number, size, parts, and the like of a face may be detected in a similar manner using a publicly-known machine learning method. The type of subject is not limited to human faces, and animals, vehicles, and the like can also be detected.

As described above, subject information can be detected by performing image analysis on image data from a live view display or which is played back and extracting feature amounts of the image data. Although the present embodiment describes face information as the subject information, there are various other types of subject information, such as red-eye determination, eye detection, closed eye detection, smile detection, and the like.

Note that face AE, face FE, and face WB can be performed at the same time as the face AF. "Face AE" refers to optimizing the exposure of the entire screen according to the brightness of the detected face. "Face FE" refers to adjusting the flash central to the detected face. "Face WB" refers to optimizing the WB of the entire screen according to the color of the detected face.

Figure 5:
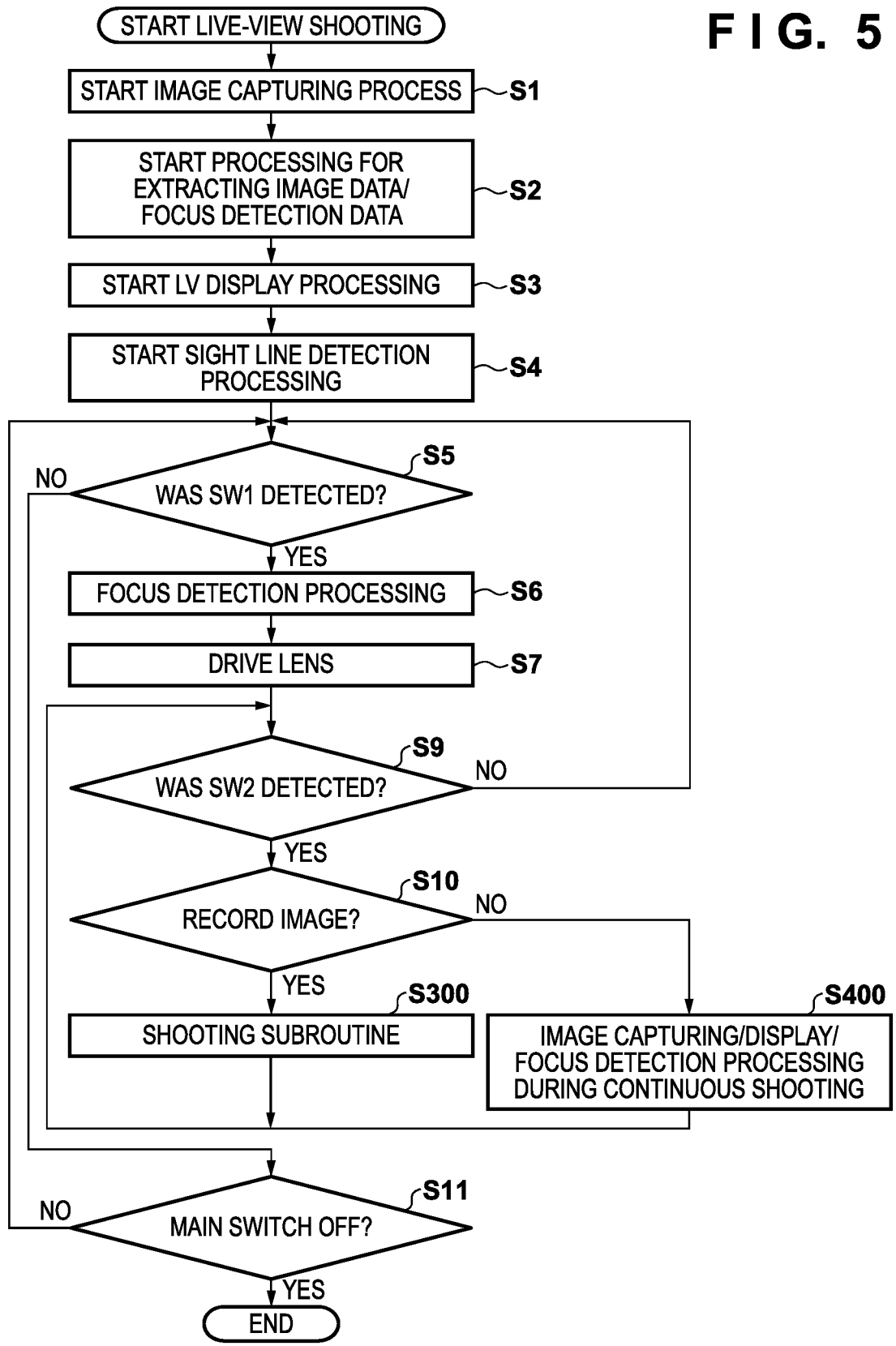
FIG. 5 is a flowchart illustrating processing pertaining to focus detection, sight line detection, and shooting operations by the digital camera 100.

Sight Line Detection and Shooting Operations Sight line position detection processing will be described next with reference to FIG. 5. FIG. 5 is a flowchart illustrating processing pertaining to focus detection, sight line detection, and shooting operations by the digital camera 100. The processing in this flowchart corresponds to processing performed during live-view shooting, in which the user performs shooting operations in a live-view state (a moving image shooting state) such as a shooting standby state, and is performed primarily by the system control unit 50.

In step S1, the system control unit 50 starts image capturing processing. From step S1, the image capturing processing is repeated and captured image data is obtained. In the image capturing processing, the system control unit 50 drives the image capturing unit 22 and obtains the captured image data. The obtained captured image data corresponds to a detection/display image rather than a recording image (described later), and is thus smaller in size than a recording image. An image having a resolution sufficient for focus detection, subject detection, live view display, and the like is obtained in the image capturing processing performed in step S1. Here, the drive operations are performed to shoot a moving image for live view display, and thus the system control unit 50 captures the image using what is known as an electronic shutter, in which charges are accumulated and read out for a time corresponding to a framerate for the live view display. The live view display performed here is for the user to confirm the shooting range, shooting conditions, and the like, and may therefore be, for example, 30 frames/second (a shooting interval of 33.3 ms), 60 frames/second (a shooting interval of 16.6 ms), and the like.

In step S2, the system control unit 50 starts processing for extracting image data and focus detection data. From step S2 onward, the extraction processing is executed each time captured image data is obtained through the image capturing processing started in step S1. In the extraction processing, the system control unit 50 obtains the focus detection data obtained from the first focus detection pixel and the second focus detection pixel from the captured image data obtained through the image capturing processing performed in step S1. The system control unit 50 also generates a captured image signal by adding the signals output from the first focus detection pixel in the second focus detection pixel, and obtains image data resulting from applying color interpolation processing and the like using the image processing unit 24. In this manner, both image data and focus detection data can be obtained in a single instance of shooting. If the pixel configuration is such that the image capturing pixel, the first focus detection pixel, and the second focus detection pixel are provided separately, the system control unit 50 obtains the image data having performed interpolation processing and the like for the focus detection pixels.

In step S3, the system control unit 50 starts live view display processing (LV display processing). From step S3 onward, the LV display processing is executed each time image data is obtained through the extraction processing started in step S2. In the LV display processing, the system control unit 50 generates a live view display image using the image processing unit 24, on the basis of the image data obtained through the extraction processing performed in step S2, and displays the live view display image in the display unit 28. Note that the live view display image is an image reduced to match the resolution of the display unit 28, for example, and reduction processing can be performed by the image processing unit 24 when generating the image data in the extraction processing performed in step S2. In this case, the system control unit 50 displays the image data obtained in the extraction processing performed in step S2 in the display unit 28. As described above, shooting and display are performed at a predetermined framerate during the live view display, and the user can therefore adjust the composition, exposure conditions, and the like of the shot while viewing the display unit 28. Additionally, as described above, in the present embodiment, a person's face, an animal, and the like can be detected as a subject. In the LV display processing, the system control unit 50 displays a live view image, and also displays a frame or the like indicating a region of the detected subject.

In step S4, the system control unit 50 starts sight line detection processing. From step S4 onward, the system control unit 50 repeatedly obtains, at predetermined time intervals, information indicating the position of the display unit 28 the user (photographer) is observing (sight line position information) using the sight line input operation unit 401, in association with the displayed image which the user is observing. The system control unit 50 also displays the detected sight line position in the display unit 28 in order to notify the user. The sight line position detected in step S4 has error with respect to the position of the subject intended by the user due to a variety of factors. In addition, although there is variation from person to person, there is a delay of several tenths of a second between the time a human sees an intended subject and the time the eye starts moving. In parallel with the processing illustrated in FIG. 5, the system control unit 50 performs processing for suppressing the influence of such error, delay time, and the like (described later with reference to FIG. 6).

In step S5, the system control unit 50 detects whether the first shutter switch 62 (SW1), which indicates the start of shooting preparations, is on/off. The system control unit 50 can detect on/off in two levels according to how much the shutter button 61 is depressed, and SW1 being on/off corresponds to the first stage of the shutter button 61 being on/off. If SW1 is not detected as being on (or is detected as being off) in step S5, the system control unit 50 moves the processing to step S11. On the other hand, if SW1 is detected as being on in step S5, the system control unit 50 moves the processing to step S6.

In step S6, the system control unit 50 performs focus detection processing (setting a focus detection region and performing focus detection). The focus detection processing in step S6 is repeatedly executed each time the live view image is obtained, until it is determined in step S5 that SW1 is off.

Figure 6:
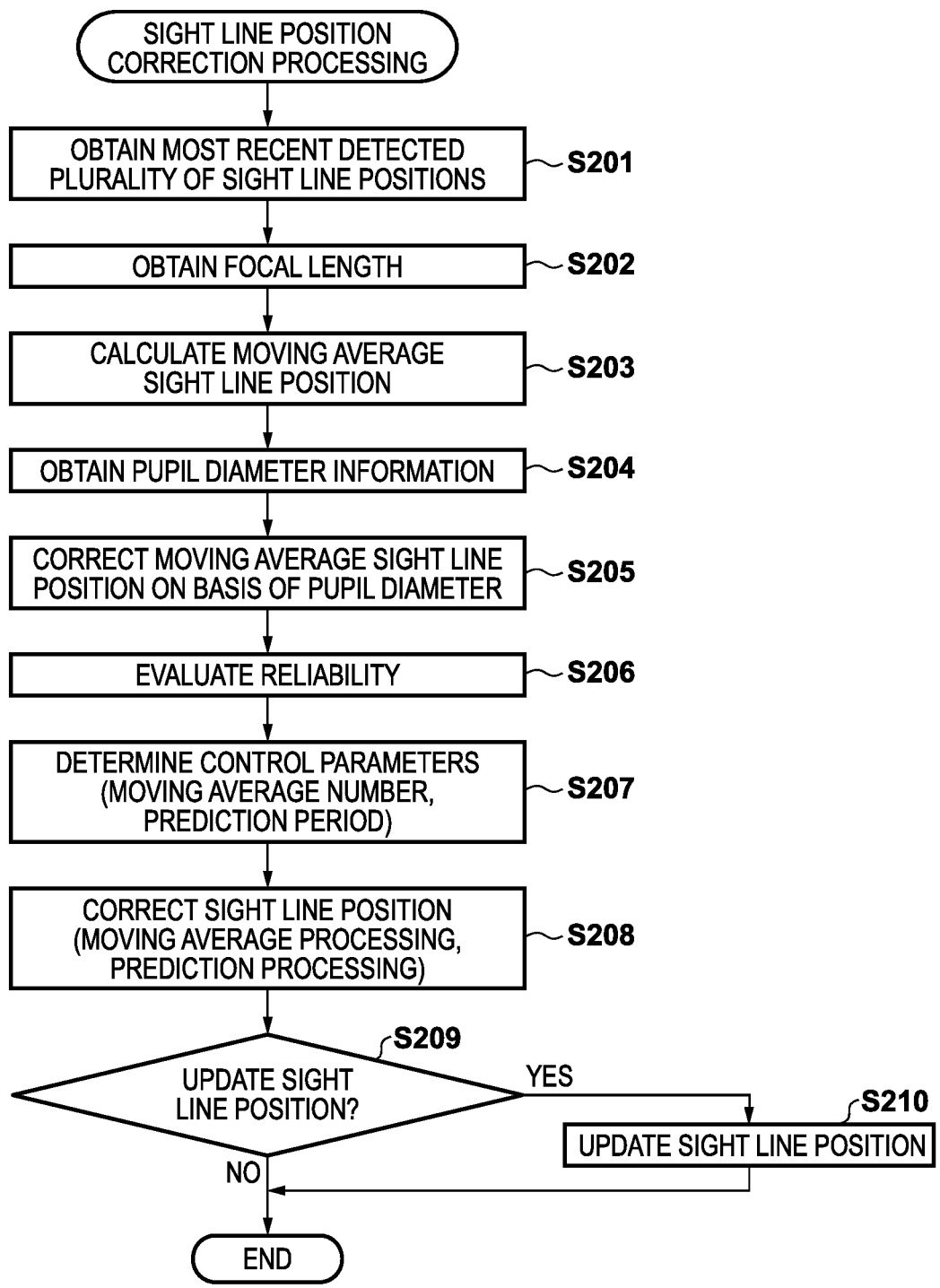
FIG. 6 is a flowchart illustrating sight line position correction processing.

In the focus detection processing, the system control unit 50 sets the focus detection region using both a sight line position detected through the sight line detection processing started in step S4 and corrected through the processing illustrated in FIG. 6, and the subject position detected through the subject detection processing included in the LV display processing started in step S3.

Then, the system control unit 50 finds a defocus amount and a defocus direction for each focus detection region using the focus detection data corresponding to the set focus detection region. The present embodiment assumes that the system control unit 50 generates focus detection image signals, calculates an amount of shift between the focus detection image signals (a phase difference), and performs processing for finding the defocus amount and the defocus direction from the calculated amount of shift.

The system control unit 50 performs shading correction and filter processing on a first focus detection signal and a second focus detection signal obtained as the focus detection image signals corresponding to the focus detection region, and reduces a difference in light amount between the pair of signals as well as extracting a spatial frequency signal for phase detection. Next, the system control unit 50 performs shift processing for shifting the post-filter processing first focus detection signal and second focus detection signal relatively in a pupil division direction, and calculates a correlation amount representing a degree to which the signals match.

A kth first focus detection signal and second focus detection signal after the filter processing are represented by $A(k)$ and $B(k)$, respectively, and the range of a number k corresponding to the focus detection region is represented by W. A shift amount from the shift processing is represented by $s_1$, and a shift range of the shift amount $s_1$ is represented by $\Gamma 1$. Such being the case, a correlation amount COR is calculated through the following Formula (1).

$$COR(s_1) = \Sigma_{k \in W} |A(k) - B(k-s_1)|  s_1 \in \Gamma 1 \quad (1)$$

Through the shift processing of the shift amount $s_1$, the system control unit 50 generates a shift subtraction signal by associating and subtracting the kth first focus detection signal $A(k)$ and a $k-s_1$th second focus detection signal $B(k-s_1)$. The system control unit 50 calculates an absolute value of the generated shift subtraction signal, finds the sum of the numbers k in the range W corresponding to the focus detection region, and calculates a correlation amount COR $(s_1)$. If necessary, the system control unit 50 may add the correlation amounts, which are calculated for each row, over a plurality of rows for each shift amount.

Next, from the correlation amount, the system control unit 50 calculates, through sub-pixel computation, a shift amount of a real number value that brings the correlation amount to a minimum value, and takes that shift amount as an image shift amount p1. The system control unit 50 then detects the defocus amount by multiplying the calculated image shift amount p1 by a conversion coefficient K1, which depends on the image height of the focus detection region, the F value of the imaging lens (the optical imaging system), and the exit pupil distance.

In step S7, the system control unit 50 performs lens driving on the basis of the defocus amount detected in the selected focus detection region. Here, if the detected defocus amount is smaller than a predetermined value, it is not absolutely necessary to perform the lens driving.

In step S9, the system control unit 50 detects whether the second shutter switch 64 (SW2), which indicates a shooting start instruction, is on/off. A release (shooting trigger) switch, which is part of the operation unit 70, is capable of detecting on/off in two levels according to how much the switch is depressed, and the aforementioned SW2 corresponds to the second level of on/off of the release (shooting trigger) switch. If SW2 is not detected to be on in step S9, the system control unit 50 returns to step S5 and detects whether SW1 is on/off.

In step S9, the system control unit 50 determines whether or not SW2 has been detected as being on. When SW2 has been detected as being on, the processing moves to step S10, whereas when SW2 has not been detected as being on, the processing returns to step S5.

In step S10, the system control unit 50 determines whether or not to record an image. In the present embodiment, the system control unit 50 switches image obtainment processing during continuous shooting between processing for recording images and processing for display/focus detection. The switching may be alternating, e.g., the processing for obtaining an image for display/focus detection may be performed once every three times or the like. This makes it possible to performed highly-accurate focus detection without drastically reducing the number of shots per unit of time. If it is determined that an image is to be recorded, the processing moves to step S300, whereas if not, the processing moves to step S400.

In step S300, the system control unit 50 obtains an image for recording by executing a shooting subroutine. Then, the determination of step S9 (i.e., the determination as to whether or not to continue continuous shooting) is made again.

In step S400, the system control unit 50 executes image capturing/display/focus detection processing during continuous shooting. The details of the image capturing/display/focus detection processing during continuous shooting are the same as the details of the processing in steps S1 to S3 and S6. However, the system control unit 50 adjusts the display period, display refresh rate (interval), display delay, and the like of the live view image as appropriate according to the shooting framerate of the continuous shooting, the recording image generation processing, and the like.

As described in the present embodiment, the user's sight line position is significantly affected when the display period, the refresh rate, and the display delay of the display image change during continuous shooting. In the present embodiment, the system control unit 50 processes the sight line position and controls the detection processing in light of the fact that error occurs in the detected sight line position depending on the state and switching of the display specifications mentioned above. This makes it possible to obtain a highly-accurate sight line position regardless of changes in display specifications. As described above, the obtained sight line position information is used to set the focus detection region, associate the focus detection region with a detected subject region, and the like. After the process of step S400, the determination of step S9 (i.e., the determination as to whether or not to continue continuous shooting) is made again.

If SW1 is not detected as being on (or is detected as being off) in step S5, the process of step S11 is performed. In step S11, the system control unit 50 determines whether or not a main switch has been detected as being off. If the main switch has been detected as being off, the processing of this flowchart ends. If the main switch is not detected as being off, the processing returns to step S5.

Sight Line Position Correction Processing Sight line position correction processing will be described next with reference to FIG. 6. FIG. 6 is a flowchart illustrating sight line position correction processing. The processing in this flowchart is executed in parallel primarily by the system control unit 50, after the start of the sight line detection processing performed in step S4 in FIG. 5.

In step S201, the system control unit 50 obtains a plurality of sight line positions detected through the most recent plurality of sight line detection processes. The number of sight line positions obtained here is a number required for moving average processing performed in steps S203 and S208, which will be described later.

In step S202, the system control unit 50 obtains focal length information of the shooting lens.

In step S203, the system control unit 50 calculates a moving average sight line position by performing moving average processing using the plurality of sight line positions. Here, the number of data (the number of sight line positions) for the moving average is a predetermined number (e.g., 5). By calculating the moving average sight line position, an oscillation component of the sight line position caused by involuntary eye movement during fixation of the user's sight line can be reduced.

In step S204, the system control unit 50 detects a pupil diameter for when the user's sight line position is detected.

In step S205, the system control unit 50 corrects the moving average sight line position on the basis of the pupil diameter. This correction is necessary because the size of the human pupil varies with the intensity of the light entering the eye, and sight line detection error varies according to the size of the pupil. Since the correction amount here varies depending on the moving average sight line position, the system control unit 50 may use the moving average sight line position to optimize the correction amount. In the present embodiment, the moving average sight line position obtained in step S203 is used instead of the sight line position obtained in step S201 in order to stabilize the correction result.

In step S206, the system control unit 50 evaluates the reliability of the sight line position using the focal length obtained in step S202 and the moving average sight line position obtained in step S203.

Figure 7:
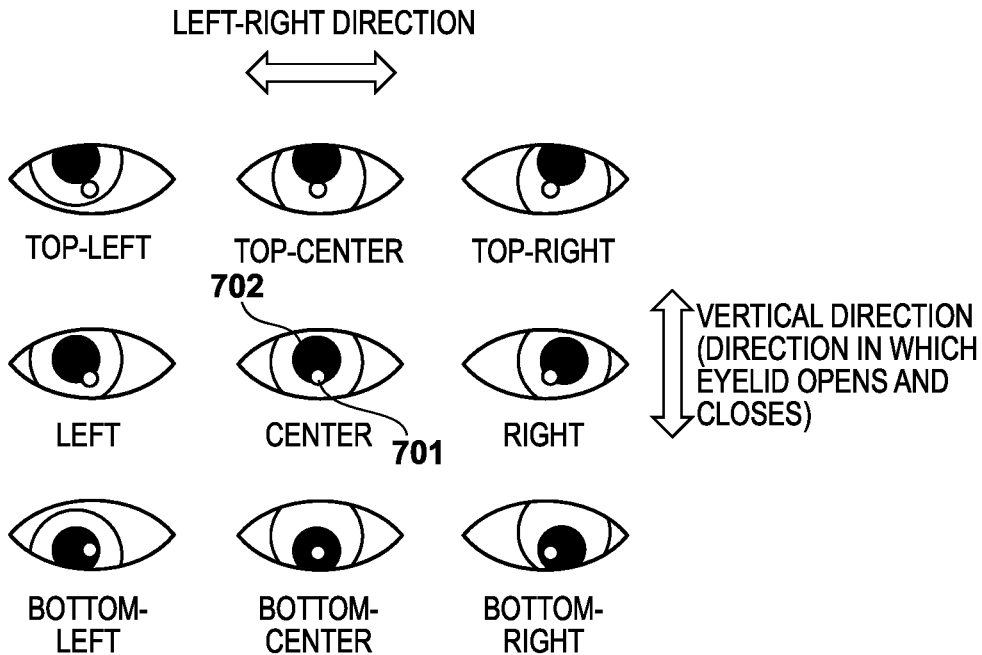
FIG. 7 is a schematic diagram illustrating a relative relationship between a pupil center and a Purkinje image for each of sight line directions.
Figure 9:
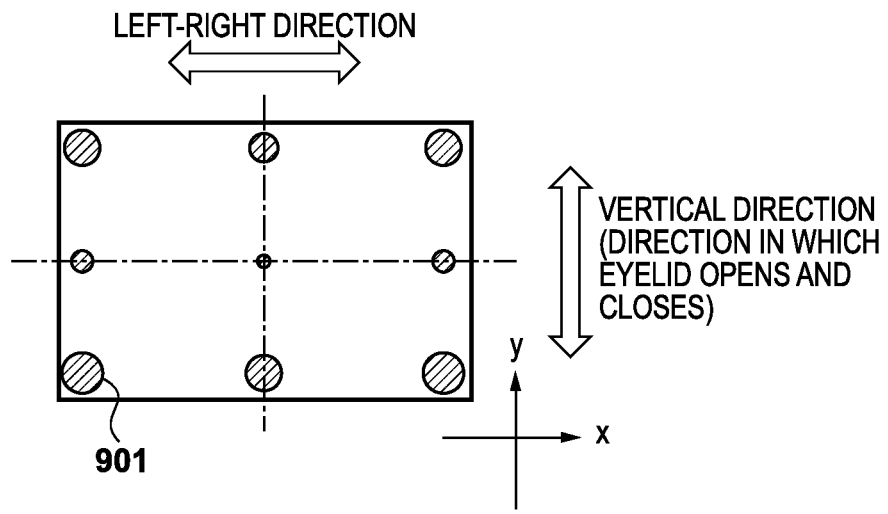
FIG. 9 is a diagram conceptually illustrating an amount of variation in a sight line position according to the sight line position when a user looks at a single point through an electronic viewfinder.

The evaluation of the reliability of the sight line position will be described with reference to FIGS. 7 and 9. FIG. 7 is a schematic diagram illustrating a relative relationship between a pupil center and a Purkinje image for each of sight line directions. 701 indicates the Purkinje image and 702 indicates the pupil. FIG. 9 is a diagram conceptually illustrating an amount of variation in the sight line position according to the sight line position when the user looks at a single point through an electronic viewfinder. 901 indicates the amount of variation in the sight line position when the user gazes at a single point at a lower-left sight line position.

In general, a sight line detection sensor (e.g., the sight line input operation unit 401 indicated in FIGS. 4A and 4B) is calibrated to a center position and is therefore designed to provide the best detection accuracy at the center position. The corneal reflection method, which detects and calculates a change in the relative positional relationship between the pupil center and the Purkinje image, is a commonly known method for detecting the sight line position. However, this detection method has the problem that the detection accuracy varies depending on the sight line position. The reason for this is that near-infrared light used to obtain the Purkinje image is emitted to a location slightly offset from the center of the pupil due to layout issues on the sensor side, and the emitted light is obliquely incident on the front of the eye, which results in the Purkinje image being observed at a location offset from the center of the eye. In addition to this issue, there is also an issue in that there is anisotropy in the change in sight line detection accuracy according to the sight line position. One reason for this is that, as illustrated in FIG. 7, when the pupil center moves in the direction in which the eyelid opens and closes (the vertical direction), part of the pupil is hidden by the eyelid, which makes it more likely that the pupil center detection accuracy will drop. Accordingly, as illustrated in FIG. 9, the sight line position detection accuracy is higher in the left-right direction than in the up-down direction relative to the center position.

The sight line detection accuracy decreases due to the structure of the sight line detection sensor as described above. Involuntary eye movement during fixation can be given as an additional human-caused item that affects the sight line detection accuracy. With respect to the structure of the eye, except in cases of strabismus, the external ocular muscles are best balanced, and involuntary eye movement during fixation is suppressed the most, when the eye is looking straight ahead. The external ocular muscles are composed of the superior rectus muscle, the inferior rectus muscle, the external rectus muscle, the medial rectus muscle, the superior oblique muscle, and the inferior oblique muscle, and involuntary eye movement during fixation increases as the forces that cause these muscles to be used become unbalanced. With respect to up-down and left-right anisotropy, there are significant differences among individuals, and thus no firm theories have been established at present. However, the more the sight line position shifts from a forward gaze state, the forces of the muscles constituting the external ocular muscles become unbalanced, which increases involuntary eye movement during fixation. In addition, it is thought that changing the sight line position in an oblique direction rather than the up, down, left, or right direction causes the forces of the muscles constituting the external ocular muscles to become unbalanced, which increases involuntary eye movement during fixation. As described above, involuntary eye movement during fixation also changes according to the sight line position, and there are large differences among individuals. Therefore, obtaining the magnitude of involuntary eye movement during fixation in personal data at each sight line position during calibration makes it possible to improve the sight line detection accuracy.

As described above, the variation in sight line detection accuracy according to the sight line position is determined by a combination of variation caused by the structure of the sight line detection sensor and variation caused by involuntary eye movement during fixation in humans. To obtain a highly-accurate sight line position taking these factors into account, it is necessary to optimize the sight line position correction processing in later stages on the basis of the reliability of the detected sight line position.

As a method for obtaining the reliability of the sight line position, a method is conceivable in which sight line information data pertaining to a plurality of sight line positions for a plurality of people is obtained in advance, variance data for each sight line position is organized, and the reciprocal thereof is found and used as a reliability evaluation value for the sight line information. By taking the reciprocal of the variance data, if the variance data is low, the variance of the sight line position is low as well, with a stable value (high reliability), which increases the value of the reliability. Conversely, if the variance data is high, the variance of the sight line position is high as well, with an unstable value (low reliability), which reduces the value of the reliability.

Additionally, as the focal length increases, the subject being shot will blur more due to the user's hand shaking. If the user's sight line follows the blurred subject, the sight line position will oscillate, and the reliability may therefore be calculated taking into account the focal length. Specifically, the reliability may be evaluated as being higher when the focal length is low, and lower when the focal length is high.

In addition to the foregoing, the reliability may be evaluated by taking into account the fact that the reliability of the sight line position obtained from the sight line detection sensor changes depending on the extent to which the eyelid is open. The reason why the reliability of the sight line position changes depending on the extent to which the eyelid is open is similar to the reason why the sight line detection accuracy differs depending on the sight line position, i.e., the eyelid hides part of the pupil, which causes a drop in the detection accuracy. The change in reliability of the sight line position according to the extent to which the eyelid is open can be detected using the sight line detection sensor. When the change in reliability of the sight line position due to the extent to which the eyelid is open cannot be detected by the sight line detection sensor, the system control unit 50 may use a different sensor to detect the extent to which the eyelid is open and evaluate the reliability.

In light of the foregoing, in step S206, the system control unit 50 evaluates the reliability on the basis of at least one of the sight line position, the focal length, and the extent to which the eyelid is open. The sight line position used here is the moving average sight line position corrected in step S205.

For example, the system control unit 50 determines the reliability to be lower as the sight line position moves away from the center of the display unit 28. Additionally, the system control unit 50 determines the reliability to be lower when the sight line position is a predetermined distance away from the center of the display unit 28 in the direction in which the user's eyelid opens and closes than when the sight line position is the same predetermined distance away from the center of the display unit 28 in a direction orthogonal to the direction in which the eyelid opens and closes. The system control unit 50 determines the reliability to be lower as the focal length of the optical imaging system increases.

Note that the processing of steps S204 and S205 can be omitted. In this case, in step S206, the system control unit 50 uses the moving average sight line position obtained in step S203 instead of the moving average sight line position corrected in step S205. The processing of step S203 can be omitted as well. In this case, in step S206, the system control unit 50 uses the sight line position obtained in step S201 instead of the moving average sight line position corrected in step S205.

In step S207, the system control unit 50 sets control parameters for correcting the sight line position on the basis of the reliability obtained in step S206. The sight line position correcting processing performed in the present embodiment is assumed to include both moving average processing and prediction processing, but instead may include only one of the moving average processing and the prediction processing. As the control parameters for the moving average processing, the system control unit 50 determines a moving average number n (a data number of the moving average). The system control unit 50 also determines a prediction period $t_{prediction\ period}$. The relationship between the reliability and the control parameter will be described later in the descriptions of the processing of step S208.

Delay time caused by the moving average processing and the delay time from when a human sees an object to when the sight line moves can be given as reasons why the prediction processing is necessary. Accordingly, as the prediction processing, the system control unit 50 performs feed-forward control for compensating for these delay times.

In step S208, the system control unit 50 performs processing for correcting the sight line position (the moving average processing and the prediction processing) on the basis of the control parameters determined in step S207. A method of deriving an approximation function from historical information of the sight line position and correcting the function, a method of using position information of starting and end points to perform position-speed control, or the like are conceivable as methods for predicting the sight line position. What should be taken into account in the prediction processing is that the sight line position to be used takes oscillatory values due to the influence of involuntary eye movement during fixation, and it is therefore necessary to derive a sight line prediction amount through appropriate low-pass processing on the basis of the reliability obtained in step S206. Although moving average processing is conceivable as a typical method for performing low-pass processing on the sight line information, a greater moving average number leads to an increase in delay time with respect to a change in the sight line, and there is thus a tradeoff with responsiveness. A method that determines the moving average number using the reliability of the sight line position is therefore effective. In other words, in the aforementioned step S207, the system control unit 50 reduces the moving average number n in order to prioritize responsiveness when the reliability is high, and increases the moving average number n in order to prioritize suppressing oscillation components when the reliability is low. The present embodiment will describe a case where the sight line prediction is performed by deriving a moving average and a first-order approximation function from the historical information of the sight line positions. However, as described with reference to step S207, the system control unit 50 may execute only one of the moving average processing and the prediction processing.

Figure 8A:
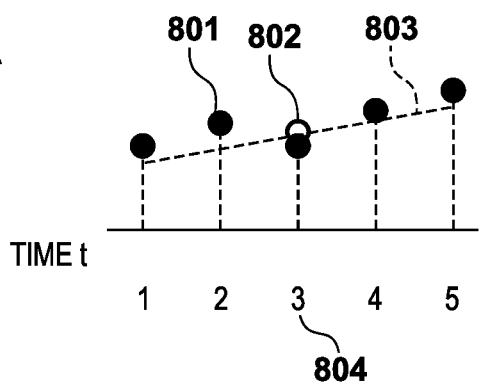
FIGS. 8A and 8B are conceptual diagrams illustrating moving average processing and prediction processing in an x direction when a moving average number n=5 and $t_{prediction\ period}=3$.
Figure 8B:
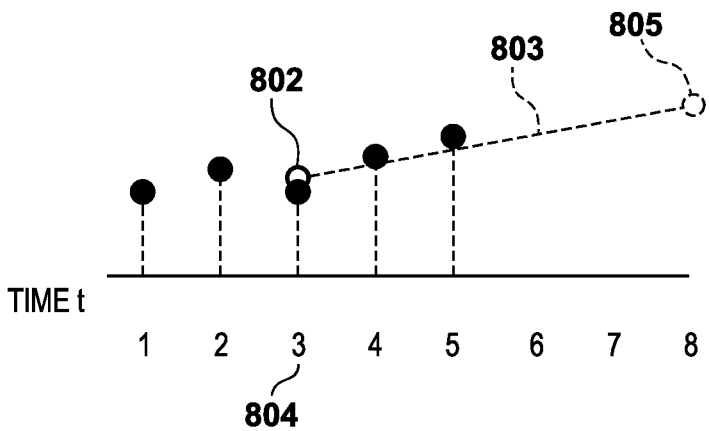

FIGS. 8A and 8B are conceptual diagrams illustrating moving average processing and prediction processing in an x direction when the moving average number n=5 and $t_{prediction\ period}$=3. Here, the moving average processing is performed on the basis of the sight line position obtained in step S201.

In FIGS. 8A and 8B, 801 indicates the sight line position at time t2, 802 indicates an average value of the sight line positions from times t1 to t5 (the moving average sight line position), 803 indicates a slope of the sight line positions from times t1 to t5 calculated through the least-squares method (a rate of variation in the sight line position), and 804 indicates a moving average center of gravity time. 805 indicates a sight line position predicted using the moving average sight line position 802 and the slope 803.

A moving average sight line position $X_5$ at time t=5 can be calculated using Formula (2).

$$X_5 = \sum_{k=1}^{n} \frac{x_k}{n} \quad (2)$$

Next, a slope $a_x$ in the x direction of the sight line position can be calculated using Formula (3).

$$a_X = \frac{n\sum_{k=1}^{n} X_k \times k - \sum_{k=1}^{n} X_k \times \sum_{k=1}^{n} k}{n\sum_{k=1}^{n} k^2 - (\sum_{k=1}^{n} k)^2} \quad (3)$$

FIG. 8B illustrates an overview of a case where the sight line position is predicted when time t=8, using the result from FIG. 8A. At time t=5 ($t_{present}$), a predicted sight line position X's at time t=8 ($t_{prediction}$) can be calculated using Formula (7) using a moving average center of gravity time $t_{moving\ average\ center\ of\ gravity}$, a moving average center of gravity correction time $t_{moving\ average\ center\ of\ gravity\ correction}$, and a prediction correction time $t_{prediction\ correction}$ expressed in Formulas (4) through (6), as well as a slope $a_x$. A term obtained by multiplying the slope $a_x$ in Formula (7) by $t_{prediction\ correction}$ is a correction amount resulting from the sight line prediction.

$$t_{moving\ average\ center\ of\ gravity} = \sum_{k=current\ time-n+1}^{n} \frac{k}{n} = \sum_{k=1}^{5} \frac{k}{5} = 3 \quad (4)$$

$$t_{moving\ average\ center\ of\ gravity\ correction} = \quad (5)$$
$$t_{current} - t_{moving\ average\ center\ of\ gravity} = 5 - 3 = 2$$

$$t_{prediction\ correction} = \quad (6)$$
$$t_{prediction} - t_{current} + t_{moving\ average\ center\ of\ gravity\ correction} =$$
$$8 - 5 + 2 = 5$$

$$X'_8 = X_5 + a_x \times t_{prediction\ correction} \quad (7)$$

Note that $t_{prediction} = t_{present} + t_{prediction\ period}$. $t_{prediction\ period}$ is a period of time corresponding to the delay from when a human sees a subject to when sight line movement starts, and can be determined through experimentation or the like. Assume here that $t_{prediction\ period}$=3. In this manner, $t_{prediction\ period}$ may be a fixed value. However, as described with reference to step S207, the system control unit 50 may determine $t_{prediction\ period}$ on the basis of the reliability of the sight line position. When the reliability of the sight line position is low, the correction component from the sight line prediction is more likely to contain error. As such, the system control unit 50 can reduce the error by making $t_{prediction\ period}$ smaller than the value corresponding to the aforementioned delay time (i.e., predicting a closer future sight line position the lower the reliability is).

The foregoing has described the time and the number of sight line positions as having the same resolution to facilitate understanding. In actual use cases too, if the number of sight line position acquisitions per unit of time is known, the sight line prediction can be performed using a moving average calculated using Formulas (2) through (7).

In addition, although the foregoing descriptions use only the x direction, it is possible to calculate the predicted sight line position in the y direction as well.

Additionally, although the foregoing has discussed a case where the sight line prediction is performed using sight line positions obtained consecutively, there are cases where the sight line position cannot be obtained partially, due to reasons such as the eye blinking or closing while the sight line position is being obtained. Even in such a case, the sight line prediction processing can be performed by taking into account the sight line position at the timing when the sight line position could not be obtained and appropriately associating the obtained sight line information with that timing, and it is not necessarily the case that the sight line prediction cannot be performed unless consecutive sight line positions are used.

In step S209, the system control unit 50 compares the new sight line position (the corrected sight line position calculated in step S208) with the original sight line position stored in the non-volatile memory 56, and determines whether or not to update the original sight line position. If a difference between the new sight line position and the original sight line position is greater than or equal to a threshold, in step S210, the system control unit 50 updates the original sight line position stored in the non-volatile memory 56 to the new sight line position. Conversely, if the difference is less than the threshold, the system control unit 50 does not update the sight line position, and ends the processing of the flowchart.

The reason for providing the determination to update the sight line position is that even if the correction processing is optimized by increasing or reducing the moving average number on the basis of the reliability, the component of the sight line position oscillating despite the subject not moving cannot be completely eliminated. Providing a dead zone for the update makes it possible to further suppress the oscillation component. In addition, in a case such as where the sight line position is displayed continuously, even if the user thinks that the sight line position is not moving, the sight line position is still moving slightly due to involuntary eye movement during fixation or the like. As such, it is useful to provide a determination threshold for updating the sight line position in order to reduce the discrepancy between the user's intentions and the result of the sight line detection. In the determination to update the sight line position, adjustments may be made on the basis of the results of the reliability evaluation made in step S206, such as making the threshold lower (reducing the dead zone) when the reliability is high and making the threshold higher (expanding the dead zone) when the reliability is low.

Variation on Sight Line Position Correction Processing

In the above-described sight line position correction processing, the configuration is such that the sight line position prediction processing is performed using an approximation function. Prediction processing using an approximation functions require a somewhat larger scale of operations when calculating the coefficients of the approximation function. Accordingly, as a variation, a configuration that predicts the sight line position using position-speed control will be described with reference to FIG. 6.

The processes of steps S201 to S207 and steps S209 to S210 are the same as in the case of using an approximation function as described above.

In step S208, the system control unit 50 performs the prediction processing using the control parameters determined in step S207. The prediction processing of this variation will be described with reference to FIGS. 8A and 8B.

In the prediction processing, the system control unit 50 uses a moving average value as a reference sight line position serving as a starting point. The reason for this is that, when performing position control, if the starting point serving as a reference oscillates, the oscillation component will increase in the sight line prediction result. The moving average sight line position can be calculated using Formula (2) above, and in the case of FIG. 8A, $X_3$ is the moving average sight line position.

Next, for the sight line position at an end point, the most recent sight line position x from before the moving average may be used in order to ensure responsiveness. Therefore, in FIGS. 8A and 8B, a sight line position $x_5$ at $t=5$ may be taken as the sight line position at the end point. If controlling the position only, the sight line prediction amount may be adjusted by multiplying the sight line positions at the starting point and the end point by a coefficient P. However, position control alone tends to overshoot when the tracking performance of the sight line prediction is improved, and it is therefore better to include speed control as well. To include speed control, the amount of variation in the most recent sight line position is necessary, and thus a term may be added by multiplying a difference between sight line positions $x_4$ and $x_5$ at times $t=4$ and $t=5$ by a coefficient D. Taking the foregoing into account, a formula for the sight line prediction using position-speed control is Formula (8).

$$X_m' = P \times \text{deviation} + D \times \text{amount of variation} = P \times (x_5 - X_5) + D \times (x_5 - x_4) \quad (8)$$

As when using an approximation function as described above, if the correction amount of the sight line position from the sight line prediction is to be reduced when the reliability is low, the system control unit 50 may reduce P in the position control term.

The present embodiment describes an example in which the sight line detection is performed by performing a simple averaging of the sight line data which is obtained. However, in light of differences and the like among sight line data, if a difference greater than a threshold is detected, the sight line detection can be performed having excluded that sight line data as an outlier, which makes it possible to suppress variations during sight line detection. Additionally, instead of averaging, an approximated curve such as the least-squares method can be obtained as the result of sight line detection for each timing. In this manner, the sight line detection results may be calculated using any statistical value.

If doing so poses no problem in terms of calculation speed and calculation scale, the calculation can be performed through median processing or Kalman filter processing instead of simply using the moving average of the sight line data. By comparing the sight line data during a predetermined period on a time axis, extracting a median value and excluding outliers, and then performing average processing, the sight line detection can be performed while suppressing variation to a greater extent.

As described thus far, according to the first embodiment, the digital camera 100 repeatedly detects the user's sight line position. Then, the digital camera 100 determines the reliability of the detected sight line position, and generates a statistical sight line position (e.g., an average sight line position) by calculating a statistical value (e.g., an average value) of a plurality of detected sight line positions. At this time, the digital camera 100 controls the number of sight line positions used to calculate a single statistical value on the basis of the reliability. For example, as the reliability decreases, the digital camera 100 controls the number of sight line positions used to calculate a single statistical value (e.g., an average value) to be greater. Accordingly, when the reliability is low, the number of averaged sight line positions is increased to suppress the effects of sight line position detection error and fluctuations caused by involuntary eye movement during fixation, and when the reliability is high, the number of averaged sight line positions is reduced to suppress delay, which improves the accuracy of the sight line detection. Additionally, the digital camera 100 estimates the speed of variation in the sight line position by, for example, using the least-squares method on the plurality of sight line positions, and predicts a future sight line position on the basis of the average sight line position and the estimated speed of variation. This compensates for the effects of delay arising when averaging a plurality of sight line positions and delay between when a human sees a subject and when sight line movement starts, which improves the accuracy of the sight line detection.

Instead of using the reliability, the digital camera 100 may control the number of sight line positions used to calculate a single statistical value on the basis of the distance of the detected sight line position from the center of the display unit 28. For example, the digital camera 100 calculates the statistical value using a larger number of sight line positions when the detected sight line positions include sight line positions at a first distance from the center of the display unit 28 than when the detected sight line positions include sight line positions at a second distance shorter than the first distance.

Second Embodiment

A second embodiment will describe a configuration in which, in the sight line position detection processing started in step S4 of FIG. 5 described in the first embodiment, the sight line position is detected using dictionary data obtained through training. Training processing for obtaining the dictionary data will also be described.

In the second embodiment, the basic configuration of the digital camera 100 is the same as in the first embodiment (see FIG. 1). The following will primarily describe areas that are different from the first embodiment.

Figure 10:
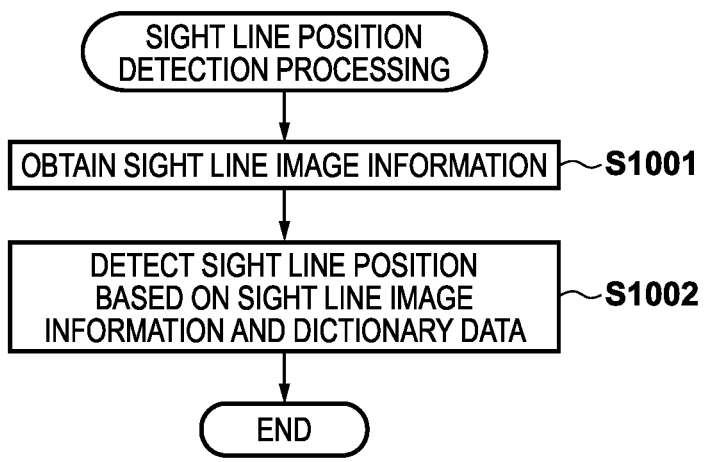
FIG. 10 is a flowchart illustrating sight line position detection processing using dictionary data.

Sight Line Position Detection Processing Using Dictionary Data FIG. 10 is a flowchart illustrating sight line position detection processing using dictionary data. It is assumed that the dictionary data is created in advance and stored in the non-volatile memory 56. A method for creating the dictionary data will be described later. As described in the first embodiment, from step S4 in FIG. 5 on, the system control unit 50 obtains the sight line position at predetermined time intervals. In the second embodiment, each instance of obtainment processing through which the system control unit 50 obtains the sight line position at each predetermined time interval corresponds to the processing of the flowchart in FIG. 10.

In step S1001, the system control unit 50 obtains eye area image information (sight line image information) using the sight line input operation unit 401.

In step S1002, the system control unit 50 detects the sight line position by performing inference on the basis of the sight line image information obtained in step S1001 and the dictionary data stored in the non-volatile memory 56. Specifically, the system control unit 50 determines whether the eye of the user included in the sight line image information is the right eye or the left eye. The determination method is not particularly limited. Next, the system control unit 50 obtains the sight line position corresponding to the sight line image information by using a deep learning CNN (convolutional neural network) included in the dictionary data.

If the sight line image information includes both of the user's eyes, the system control unit 50 may specify a right-eye region and a left-eye region in the sight line image, and detect the sight line position using dictionary data that can be used for both the left and right eyes as appropriate.

Dictionary Data Creation Method A method for creating the dictionary data used in the above-described sight line position detection processing will be described here.

When detecting sight line information (the sight line position) from the positional relationship between the pupil position of an eye and a Purkinje image, the detection results will vary depending on the sight line position, the iris diameter, the pupil diameter, and the reliability of the eye area image. Thus when creating dictionary data through training using an image of an eye, more accurate trained dictionary data can be created by performing the training in association with a sight line position, the iris diameter, the pupil diameter, and the reliability of the eye area image as related information.

In order to obtain the eye area image information related to an apparatus such as a camera, where the user looks into the viewfinder with one eye, and input the information into a trainer to create trained dictionary data, a method for collecting training data is necessary.

Some people use their right eye, while others use their left eye, when looking into the viewfinder of a camera. Normally, it is necessary to prepare training data and trained dictionary data for the right eye and the left eye individually, but it is possible to determine whether an image is a right-eye image or a left-eye image by taking into account human feature points such as the inner and outer corners of the eye. Therefore, when eye area images are input to the eye area information trainer to create the trained dictionary data, image processing is performed within the eye area information trainer, such as processing for associating data by taking human symmetry into account, horizontally inverting either the right eye or the left eye to align the eye orientation, or the like. This makes it possible to create the trained dictionary data by causing the trainer to train using training data for each of the right eye and the left eye as eye area image data that can be used for both the left and right eyes.

When performing sight line detection using the trained dictionary data that can be used for both the left and right eyes, the system control unit 50 determines whether the image is a right-eye image or a left-eye image by detecting eye area information, such as the inner and outer corners of the eye, from the eye area image (the sight line image information in step S1001). The system control unit 50 then obtains the eye area information, and obtains the sight line position, after performing pre-processing such as image inversion processing as appropriate.

Figure 11:
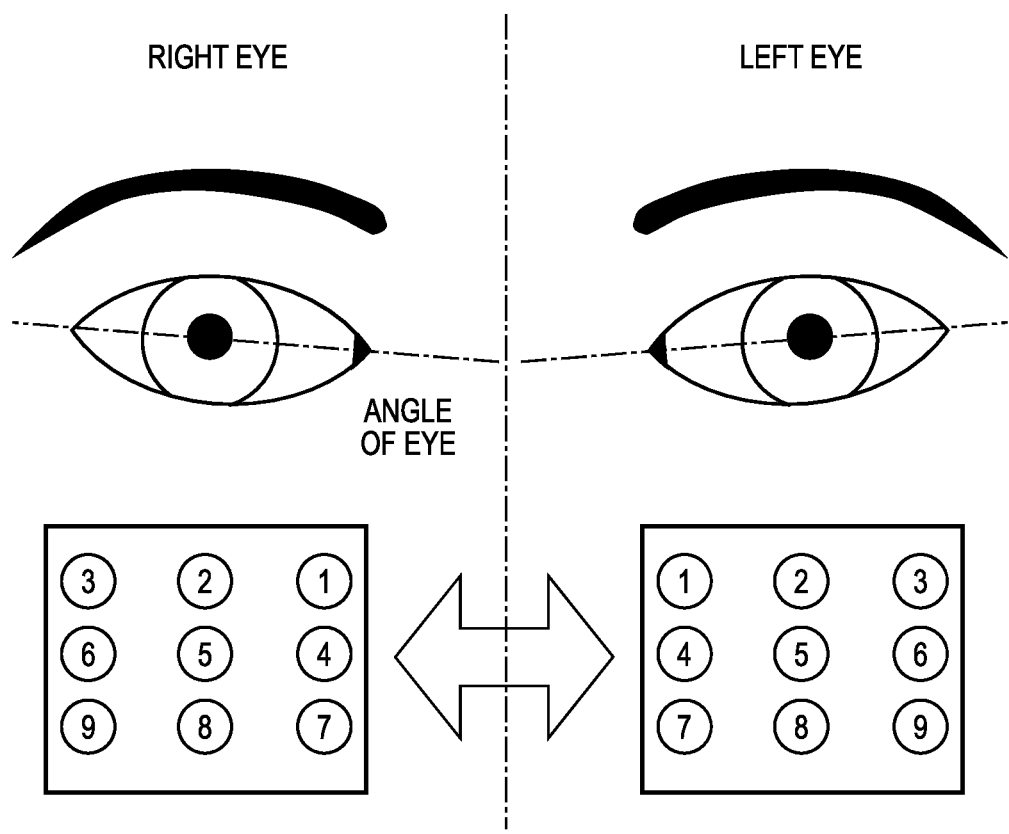
FIG. 11 is a diagram illustrating a correspondence relationship between sight line directions of left and right eyes.

FIG. 11 is a diagram illustrating a correspondence relationship between sight line directions of left and right eyes. In the case of the sight line position and the eyes, the left and right eyes are arranged and configured roughly symmetrically to the center of the body, as illustrated in FIG. 11. As such, highly-generic training data can be created by horizontally inverting the eye area images for each left and right sight line position, and creating training data on the basis of humans whose sight line positions have also been horizontally inverted. In order to create highly-generic training data, it is necessary to collect as many different types of eye area images as possible when collecting the data of eye area images. Even individual humans are not perfectly horizontally symmetrical, and furthermore have dominant eyes, and there is thus a large difference between the left and right in terms of how people look into a camera. Therefore, even if the eye area images are images of the same person's eyes, image data having different tendencies are obtained for the left and right eyes. As such, to create trained dictionary data for detecting a sight line position from a generic eye area image, more accurate and versatile sight line detection can be performed when creating trained dictionary data that can be used for both the left and right eyes taking into account horizontal symmetry, than when preparing separate data for the left and right eyes.

When creating trained dictionary data, inputting the training data into the trainer after first performing image processing taking into account feature points of the eyes makes it possible to detect even minute features. Because this is, to a certain extent, a process of deliberately deriving common points from the collected training data, it is necessary to take care not to over-train the dictionary data, but if used appropriately, the method is effective in improving the sight line information detection accuracy.

If the trained dictionary data is created using training data collected in an excessively random manner, there is a risk that the detection accuracy will be significantly reduced when data that deviates even slightly from the average is applied to the dictionary data. Therefore, this shortcoming can be compensated for by intentionally applying image processing to some of the training data before creating the trained dictionary data. Additionally, the sight line detection accuracy can be improved even further by using a plurality of dictionaries and performing the sight line detection using different dictionaries depending on the conditions. As a method for using a plurality of dictionaries for different situations, there is a method of using first dictionary data trained completely randomly and second dictionary data trained using training data in which some of the data has been intentionally subjected to image processing. Then, a method is conceivable in which when the sight line detection cannot be detected using the first dictionary data, the sight line detection is performed using the second dictionary data, or in which the sight line detection is generally detected using the first dictionary data and then detected precisely using the second dictionary data.

The purpose of the image processing will be described with reference to FIG. 11. For example, an angle of the eye can be defined by a positional relationship between the inner and outer corners of the eye, and creating dictionary data after aligning the angles of the eyes in the training data makes it easier to learn the contours of the eye, fine structure information of the eye such as the positional relationships between the iris, pupil, the inner corner of the eye, the outer corner of the eye, and the like. Also, since different races have different iris color information, it is also effective to use color information if the sight line detection sensor is capable of detecting color. Therefore, taking into account the positional relationship, shape, color, and the like in the eye structure information such as eye inner corner information, eye outer corner information, iris information, pupil information, eyelash information, eyebrow information, and the like, and performing image processing such as image size adjustment, image rotation angle adjustment, image cropping range adjustment, color adjustment, contrast adjustment, edge extraction processing (digital filter processing), and the like before creating the dictionary data, dictionary data which enables more accurate sight line detection can be created.

It is also very important to increase the amount of training data in order to increase the accuracy of the dictionary data. When collecting training data, a plurality of instances of sight line detection data are often obtained when calibrating the sight line detection sensor after the camera is turned on. Accordingly, the camera may be used as a sight line detection apparatus, and if the user of the camera consents, the eye area image, eye area feature information, and the reliability of the sight line information (sight line reliability) of the eye area image may be transmitted from the camera to a cloud server through wireless communication or the like. If the transmitted data can be used as training data, the training data can be collected efficiently. If the training data collected in this manner is additionally used for training to create trained dictionary data, and the retrained dictionary data is received by the camera and used for sight line detection, the user of the camera can shoot images using more accurate sight line detection results.

Figure 12:
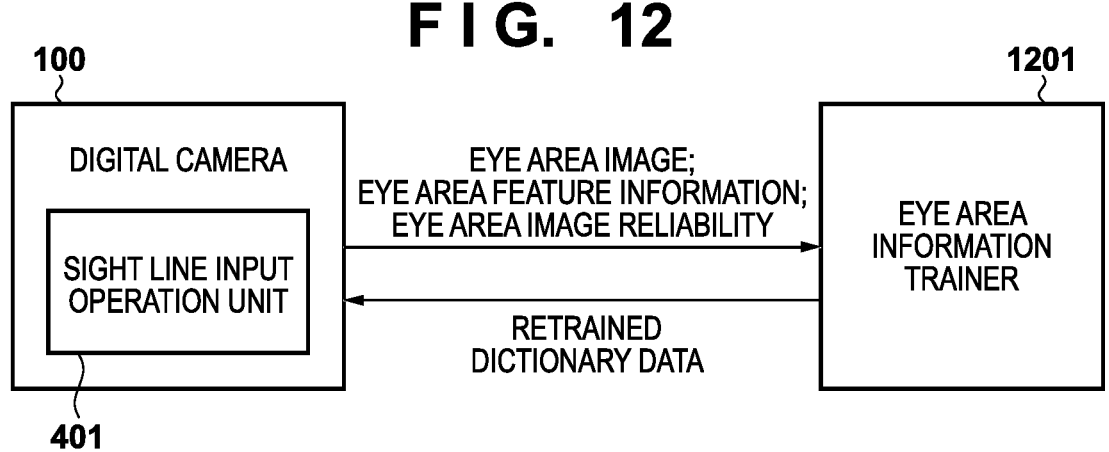
FIG. 12 is a conceptual diagram illustrating processing for generating retrained dictionary data.

FIG. 12 is a conceptual diagram illustrating processing for generating the aforementioned retrained dictionary data. An eye area information trainer 1201 generates the retrained dictionary data on the basis of the aforementioned eye area image, eye area feature information, and reliability of the sight line information (sight line reliability) in the eye area image transmitted to the cloud server.

Configuration of Eye Area Information Trainer Next, the configuration of the eye area information trainer 1201 for generating dictionary data will be described with reference to FIGS. 13A to 13D. The eye area information trainer 1201 can be implemented by an information processing apparatus such as a personal computer, for example. Alternatively, the digital camera 100 may include the eye area information trainer 1201.

Figure 13A:
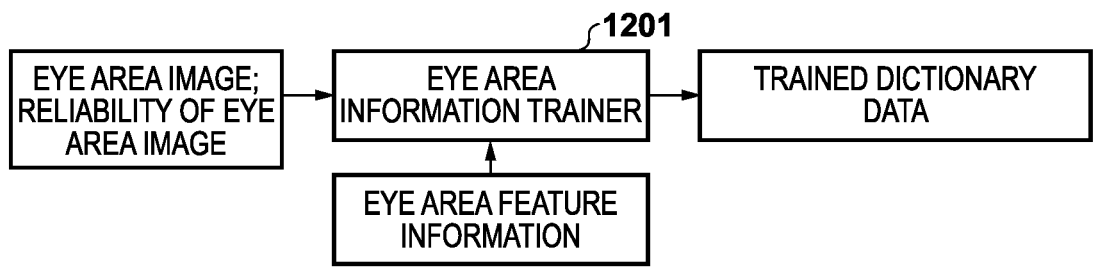
FIGS. 13A to 13D are diagrams illustrating the configuration of an eye area information trainer 1201 for generating dictionary data.

As illustrated in FIG. 13A, the eye area information trainer 1201 is input with eye area features such as the sight line position, eye inner corner information, eye outer corner information, iris information, pupil information, eyelash information, and eyebrow information, as well as the prepared eye area images that are associated with the reliability of the eye area image information. The eye area information trainer 1201 performs training on the basis of this input data, and trained dictionary data is created as an output.

Figure 13B:
Figure 13C:
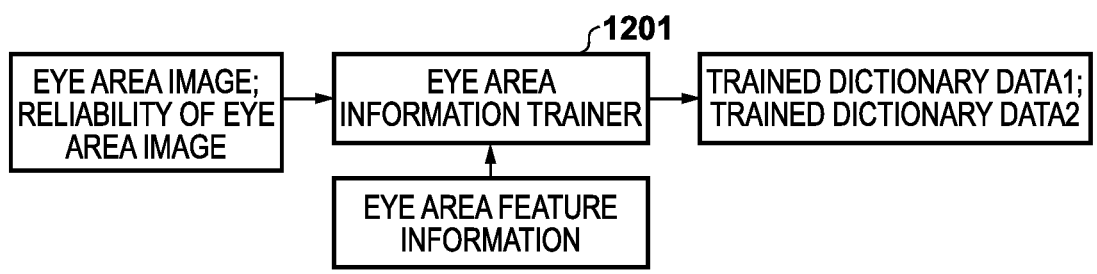
Figure 13D:
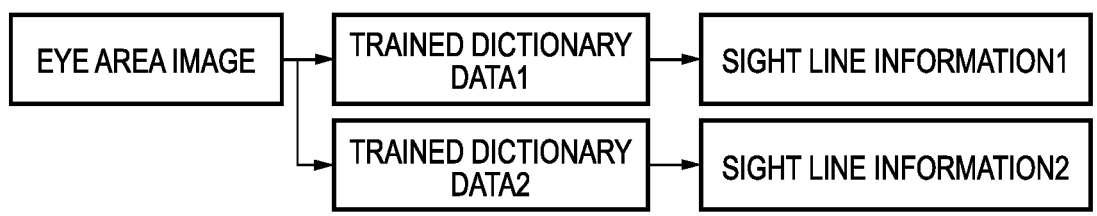

As illustrated in FIG. 13B, when an eye area image is input to this trained dictionary data, sight line information (information indicating the sight line position) is output. The reason for adding the eye area information and the reliability of the eye area image information in addition to the eye area image information as the input to the eye area information trainer 1201 is to train the sight line position by taking eye area information into account integrally during automatic training, automatically generate dictionaries trained individually for each instance of eye area information, automatically generate a plurality of dictionaries using different training methods based on the eye area information, automatically select eye area images suitable for use as training data, or the like. The following will describe a case in which the eye area information trainer 1201 trains the sight line position taking into account a plurality of instances of the eye area information. Consider a case, as illustrated in FIG. 13C, where the eye area information trainer 1201 creates a plurality of instances of trained dictionary data on the basis of the input eye area information and uses the trained dictionary data to obtain the sight line information. In this case, as illustrated in FIG. 13D, the eye area image may be passed through a plurality of instances of trained dictionary data to obtain a plurality of instances of sight line information.

Because of the large individual differences in the human eye area, the sight line detection accuracy may not be able to be satisfactorily guaranteed if the sight line detection is performed using only dictionary data that has been randomly trained by a trainer (randomly-selected trained dictionary data). Accordingly, in addition to the randomly-selected trained dictionary data, data having a high level of similarity may be selected by focusing on specific eye area features, and dictionary data trained by the trainer for each selection method (conditionally-selected trained dictionary data) may be prepared. In this case, the system control unit 50 performs the sight line detection using both the randomly-selected trained dictionary data and the conditionally-selected trained dictionary data.

Here, FIG. 7, described in the first embodiment, will be referred to again for the descriptions. As described in the first embodiment, the sight line detection by the sight line detection sensor (e.g., the sight line input operation unit 401 illustrated in FIGS. 4A and 4B) has a different level of accuracy depending on the sight line position. There is also anisotropy in the change in the sight line detection accuracy according to the sight line position.

Therefore, when creating the trained data, in addition to all-sight line position trained data obtained by training with eye area images at all sight line positions regardless of the sight line position, individual sight line position trained data obtained by classifying images according to sight line positions such as center, upper-right, and lower-left and then training with those images, as illustrated in FIG. 7, may be created.

When creating the all-sight line position trained data and the individual sight line position trained data, a configuration may be employed to make it easier to detect the eye area features (the sight line position, eye inner corner information, eye outer corner information, iris information, pupil information, eyelash information, and eyebrow information). Specifically, a training configuration may be employed in which image data having a higher spatial resolution is used for the individual sight line position trained data than for the all-sight line position trained data. When detecting the relative positional relationship between a pupil and a Purkinje image, detecting the eye area information as well makes it possible to determine the positional relationship (distance and rotation angle) between the sight line detection sensor that obtains the eye area image and the user's eye area. Continually detecting the positional relationship between the sight line detection sensor and the user's eye area makes it possible to realize precise calibration when detecting the sight line position, which is effective in realizing highly-accurate sight line position detection.

When performing sight line detection, first, the system control unit 50 performs sight line detection using the all-sight line position trained data. If the pupil or Purkinje image is optically vignetted by the eyelid or the like and the sight line detection accuracy is likely to drop (sight line positions such as the upper-right and the lower-left in FIG. 2), the system control unit 50 uses the individual sight line position trained data to detect the sight line position. This makes it possible to balance high speed and high accuracy in the sight line position detection.

The need to create trained dictionary data that takes the iris diameter into account will be described next. Unlike the pupil, the iris is not affected by environmental changes and does not change in size, and individual differences are small. It is therefore possible to obtain rough information about the distance from the eye to the sight line detection sensor (called "eye distance" hereinafter) from the size of the iris. If an optical system such as a contact lens or eyeglasses is inserted between the sight line detection sensor and the eyeball, the apparent size of the iris will change.

In an image capturing apparatus such as the digital camera 100, the eye distance is likely to fluctuate because, unlike a medical device, the head is not fixed when the sight line information is obtained. Even under such circumstances, however, highly-accurate sight line detection can be achieved by taking the size of the iris into account when performing the sight line detection.

The need to create trained dictionary data that takes the pupil diameter into account will be described next. The diameter of the human pupil varies depending on the intensity of the light entering the eye. Therefore, as the intensity of the light entering the eye changes, vignetting of the pupil by the eyelid and the like changes, and the sight line detection accuracy changes as well.

Finally, the need to create trained dictionary data by associating the reliability of the eye area images will be described. Even if the user's sight line is directed at the same position in the viewfinder, there are large individual differences in the way the eyelids open and the way the user looks into the viewfinder. Therefore, the reliability of the eye area image varies greatly due to obstructions between the eyeball and the sight line detection sensor, vignetting caused by the eyelid, and the like. For image data for training which has mixed degrees of vignetting of the pupil and iris, more accurate trained data can be generated by processing the image data while sorting the image data on the basis of whether processing is required, excluding image data, and the like. In order to efficiently sort image data for training and create highly-accurate trained dictionary data, it is necessary to automatically sort the obtained image data. Accordingly, if the sight line detection sensor can output the reliability of the sight line information, that information may also be included, or a configuration may be employed in which the reliability of the sight line in the eye area image is calculated and included before training is performed.

As described thus far, according to the second embodiment, the eye area information trainer 1201 generates trained dictionary data by performing training based on a plurality of eye area images associated with information indicating a sight line position. As this time, the eye area information trainer 1201 generates trained dictionary data that can be used for both the left and right eyes on the basis of the horizontal symmetry of the right eye and the left eye in a plurality of eye area images. This makes it possible to generate highly-accurate trained dictionary data.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-126725, filed Jul. 27, 2020 which is hereby incorporated by reference herein in its entirety.

What is claimed is:

1. A sight line position processing apparatus comprising at least one processor and/or at least one circuit including:
    a detection unit configured to repeatedly detect a sight line position of a user;
    a first determination unit configured to determine a reliability of the sight line position detected by the detection unit;
    and a generation unit configured to generate a statistical sight line position by calculating a statistical value for a plurality of sight line positions of the user, each of which is detected by the detection unit at a different time, the generation unit controlling a number of sight line positions of the user, each of which is detected at a different time, used to calculate one statistical value on the basis of the reliability,
    wherein the first determination unit determines the reliability to be lower the farther the sight line position detected by the detection unit is from a center of a display.

2. The sight line position processing apparatus according to claim 1, wherein the at least one processor and/or at least one circuit includes: an estimation unit configured to estimate a variation speed of a sight line position; and a prediction unit configured to predict a future sight line position on the basis of the statistical sight line position and the variation speed that has been estimated.

3. The sight line position processing apparatus according to claim 2,
    wherein the prediction unit predicts a sight line position closer in the future as the reliability decreases.

4. The sight line position processing apparatus according to claim 2, wherein the at least one processor and/or at least one circuit includes: a second determination unit configured to determine whether or not a difference between a sight line position stored in a storage unit and the future sight line position obtained through the prediction is greater than or equal to a threshold, the second determination unit using a higher value for the threshold as the reliability decreases; and an updating unit configured to update the sight line position stored in the storage unit to the future sight line position when the difference is greater than or equal to the threshold.

5. The sight line position processing apparatus according to claim 1,
wherein the first determination unit determines the reliability to be lower when the sight line position detected by the detection unit is a predetermined distance from the center of the display in an opening/closing direction of an eyelid of the user than when the sight line position detected by the detection unit is the predetermined distance from the center of the display in a direction orthogonal to the opening/closing direction of the eyelid of the user.

6. A sight line position processing apparatus comprising at least one processor and/or at least one circuit including: a detection unit configured to repeatedly detect a sight line position of a user; a first determination unit configured to determine a reliability of the sight line position detected by the detection unit; and a generation unit configured to generate a statistical sight line position by calculating a statistical value for a plurality of sight line positions of the user, each of which is detected by the detection unit at a different time, the generation unit controlling a number of sight line positions of the user, each of which is detected at a different time, used to calculate one statistical value on the basis of the reliability, wherein the generation unit performs control such that the number of sight line positions used to calculate the one statistical value is higher the lower the reliability is.

7. The sight line position processing apparatus according to claim 1,
wherein the statistical value is an average value.

8. The sight line position processing apparatus according to claim 1,
wherein the detection unit performs the detection through inference based on trained dictionary data.

9. An image capturing apparatus, comprising:
the sight line position processing apparatus according to claim 1; and
an image sensor.

10. The image capturing apparatus according to claim 9,
wherein the first determination unit determines the reliability to be lower the longer a focal length of an optical imaging system used by the image sensor is.

11. A training apparatus comprising at least one processor and/or at least one circuit which includes:
a training unit configured to generate trained dictionary data by performing training based on a first plurality of eye area images each associated with information indicating a sight line position,
wherein on the basis of horizontal symmetry of a right eye and a left eye in the first plurality of eye area images, the training unit:
performs image processing for horizontally inverting at least some of the first plurality of eye area images; and
generates trained dictionary data that can be used for detecting a respective sight line position for a respective eye area image, which is different from the first plurality of eye area images used for the training, in both cases where the respective eye area image corresponds to a left eye and where the respective eye area image corresponds to a right eye.

12. The training apparatus according to claim 11,
wherein the training unit generates trained dictionary data for each of sight line positions by classifying the first plurality of eye area images by sight line position and performing training for each sight line position.

13. The training apparatus according to claim 11,
wherein the training unit generates trained dictionary data for each of sight line positions by classifying, by sight line position, a second plurality of eye area images having a lower resolution than the first plurality of eye area images and each being associated with information indicating a sight line position, and performing training for each sight line position.

14. The training apparatus according to claim 11,
wherein the training unit performs training on the basis of at least one of a position, a shape, and a color of at least one of an eye inner corner, an eye outer corner, an iris, a pupil, an eyelash, and an eyebrow of an eye included in the first plurality of eye area images.

15. A sight line position processing method executed by a sight line position processing apparatus, comprising:
repeatedly detecting a sight line position of a user;
determining a reliability of the sight line position detected by the detecting; and
generating a statistical sight line position by calculating a statistical value for a plurality of sight line positions of the user, each of which is detected by the detecting at a different time, wherein the generating includes controlling a number of sight line positions of the user, each of which is detected at a different time, used to calculate one statistical value on the basis of the reliability,
wherein the determining includes determining the reliability to be lower the farther the sight line position detected by the detecting is from a center of a display.

16. A training method executed by a training apparatus, comprising:
generating trained dictionary data by performing training based on a first plurality of eye area images each associated with information indicating a sight line position, and
on the basis of horizontal symmetry of a right eye and a left eye in the first plurality of eye area images:
performing image processing for horizontally inverting at least some of the first plurality of eye area images; and
generating trained dictionary data that can be used for detecting a respective sight line position for a respective eye area image, which is different from the first plurality of eye area images used for the training, in both cases where the respective eye area image corresponds to a left eye and where the respective eye area image corresponds to a right eye.

17. A non-transitory computer-readable storage medium which stores a program for causing a computer to execute a sight line position processing method comprising:
repeatedly detecting a sight line position of a user;
determining a reliability of the sight line position detected by the detecting; and
generating a statistical sight line position by calculating a statistical value for a plurality of sight line positions of the user, each of which is detected by the detecting at a different time, wherein the generating includes controlling a number of sight line positions of the user, each of which is detected at a different time, used to calculate one statistical value on the basis of the reliability, wherein the determining includes determining the reliability to be lower the farther the sight line position detected by the detecting is from a center of a display.

18. A non-transitory computer-readable storage medium which stores a program for causing a computer to execute a training method comprising:

generating trained dictionary data by performing training based on a first plurality of eye area images each associated with information indicating a sight line position, and on the basis of horizontal symmetry of a right eye and a left eye in the first plurality of eye area images:

performing image processing for horizontally inverting at least some of the first plurality of eye area images; and generating trained dictionary data that can be used for detecting a respective sight line position for a respective eye area image, which is different from the first plurality of eye area images used for the training, in both cases where the respective eye area image corresponds to a left eye and where the respective eye area image corresponds to a right eye.

19. A sight line position processing method executed by a sight line position processing apparatus, comprising:

repeatedly detecting a sight line position of a user;

determining a reliability of the sight line position detected by the detecting; and generating a statistical sight line position by calculating a statistical value for a plurality of sight line positions of the user, each of which is detected by the detecting at a different time, wherein the generating includes controlling a number of sight line positions of the user, each of which is detected at a different time, used to calculate one statistical value on the basis of the reliability, wherein the generating includes performing control such that the number of sight line positions used to calculate the one statistical value is higher the lower the reliability is.

20. A non-transitory computer-readable storage medium which stores a program for causing a computer to execute a sight line position processing method comprising:

repeatedly detecting a sight line position of a user;

determining a reliability of the sight line position detected by the detecting; and generating a statistical sight line position by calculating a statistical value for a plurality of sight line positions of the user, each of which is detected by the detecting at a different time, wherein the generating includes controlling a number of sight line positions of the user, each of which is detected at a different time, used to calculate one statistical value on the basis of the reliability, wherein the generating includes performing control such that the number of sight line positions used to calculate the one statistical value is higher the lower the reliability is.

* * * * *